United States Patent [19]
Kurtzman et al.

[11] Patent Number: 5,952,221
[45] Date of Patent: Sep. 14, 1999

[54] ADENO-ASSOCIATED VIRUS VECTORS COMPRISING A FIRST AND SECOND NUCLEIC ACID SEQUENCE

[75] Inventors: Gary J. Kurtzman, Menlo Park; Peter C. Colosi, Alameda, both of Calif.; Jun Yoshida; Masaaki Mizuno, both of Nagoya, Japan; Hideho Okada, Pittsburgh, Pa.

[73] Assignee: Avigen, Inc., Alameda, Calif.

[21] Appl. No.: 08/812,102

[22] Filed: Mar. 5, 1997

Related U.S. Application Data

[60] Provisional application No. 60/013,209, Mar. 6, 1996.
[51] Int. Cl.$^6$ .......................... C12N 15/63; C12N 15/85; A61K 48/00
[52] U.S. Cl. ...................... 435/320.1; 514/44; 424/93.1; 435/325
[58] Field of Search .............................. 514/44; 536/23.1; 424/93; 435/320.1, 325

[56] References Cited

U.S. PATENT DOCUMENTS

| | | | |
|---|---|---|---|
| 5,252,479 | 10/1993 | Srivastava | 435/235.1 |
| 5,601,818 | 2/1997 | Freeman et al. | 424/93.21 |

FOREIGN PATENT DOCUMENTS

| | | |
|---|---|---|
| 0 690 129 A1 | 1/1996 | European Pat. Off. . |
| 4431 401 A1 | 2/1996 | Germany . |
| WO 92/05262 | 4/1992 | WIPO . |
| WO 94/21115 | 9/1994 | WIPO . |
| WO 95/07105 | 3/1995 | WIPO . |
| WO 95/09655 | 4/1995 | WIPO . |
| WO 95/13392 | 5/1995 | WIPO . |
| WO 95/14771 | 6/1995 | WIPO . |
| 95/27494 | 10/1995 | WIPO . |
| WO 95/28493 | 10/1995 | WIPO . |
| WO 95/28948 | 11/1995 | WIPO . |

OTHER PUBLICATIONS

Vieweg et al. (1995) Cancer Investigation, vol. 13(2), 193–201, 1995.
Gura (1997) Science, vol. 278, 1041–1042, Nov. 1997.
Orkin et al. (1995) "Report and Recommendations of the panel to assess the NIH investment in research on gene therapy", 1995.
Ross et al. (1996) Human Gene Therapy, vol. 7, 1781–1790, Sep. 1996.
Zhang et al. (1996) Cancer Gene Therapy, vol. 3 (1), 31–38, Jan. 1996.
Su et al. (1996) Human Gene Therapy, vol. 7, 463–470, Mar. 1, 1996.
Chen et al. (1995) Proc. Natl. Acad. Sci. USA, vol. 92, 2577–2581, 1995.
Zhang et al. (1994) Cancer Gene Therapy, vol. 1 (1), 5–13, 1994.
Tani, Kenzaburo. Gene Therapy for Cancer, 29(10) 1117–22, 1993.
Hooghe–Peters E et al., Gene Therapy, 1 Suppl 1 S80, 1994.
Finegold et al., PNAS, 92(7) 2577–81, May 2, 1995.
Taylor et al., Cancer Gene Therapy, 3 (1) 31–8, Jan. 1996.
Su et al., Human Gene Therapy, 7:463–470, Mar. 1996.
Lauret et al., "Development of Methods for Somatic Cell Gene Therapy Directed Against Viral Diseases, Using Retroviral Vectors Carrying the Murine or Human Interferon–β Coding Sequence: Establishment of the Antiviral State in Human Cells," *Human Gene Therapy* 4:567–577 (1993).
Yagi et al., "Interferon–β Endogenously Produced by Intratumoral Injection of Cationic Liposome–Encapsulated Gene: Cytocidal Effect on Glioma Transplanted Into Nude Mouse Brain," *Biochem. And Molecular Biol. Intl.* 32(1):167–171 (1994).
Zhang et al., "Gene Therapy With an ADENO–Associated Virus Carrying an Interferon Gene Results in Tumor Growth Suppression and Regression," *Cancer Gene Therapy* 3(1):31–38 (1996).
Database WPI, "Recombinant DNA and Transformed Cells Having Human Interferon Gene Used for Production of Human Interferon Having Antiviral and Antitumour Activities," *Derwent Publ. Ltd.* 1 page (1988).
Zhang et al. (1995) J. Cell. Biochem., Suppl. 21A, 422, 1995.
Anderson et al. (1995) Exp. Hematol., vol. 23 (8), 994(a), 1995.
Anderson et al. (1995) Blood, vol. 86 (10), 939, 1995.
Badie et al., "Stereotactic Delivery of a Recombinant Adenovirus into a C6 Glioma Cell Line in a Rat Brain Tumor Model," *Neurosurgery* 35(5):910–916 (1994).
Bonnekoh et al., "Inhibition of Melanoma Growth by Adenoviral–Mediated HSV Thymidine Kinase Gene Transfer," *J. of Investigative Dermatology* 104(3):313–317.
Chambers et al., "Comparison of Genetically Engineered Herpes Simplex Viruses for the Treatment of Brain Tumors in a Scid Mouse Model of Human Malignant Glioma," *Proc. Natl. Acad. Sci. USA* 92:1411–1415 (1995).
Chen et al., "Gene Therapy for Brain Tumors: Regression of Experimental Gliomas by Adenovirus–Mediated Gene Transfer In Vivo," *Proc. Natl. Acad. Sci. USA* 91:3054–3057 (1994).
Culver et al., "In Vivo Gene Transfer with Retroviral Vector–Producer Cells for Treatment of Experimental Brain Tumors," *Science* 256:1550–1552 (1992).

(List continued on next page.)

*Primary Examiner*—Deborah Crouch
*Assistant Examiner*—A.M. S. Beckerleg
*Attorney, Agent, or Firm*—Robins & Associates

[57] ABSTRACT

The use of recombinant adeno-associated virus (AAV) virions for the treatment of solid tumors is disclosed. The invention provides for the use of recombinant AAV virions to deliver an AAV vector containing a drug-susceptibility gene and a second gene capable of providing an ancillary effect to solid tumor cells. The second gene can be used to enhance the immunogenicity of the transduced tumor cell. Alternatively, the second gene can be used to provide a tumorstatic effect. The invention also provides for the use of recombinant AAV virions to deliver an interferon gene, or a tumor suppressor gene to provide a therapeutic effect in a transduced tumor cell.

6 Claims, 4 Drawing Sheets

OTHER PUBLICATIONS

DiMaio et al., "Directed Enzyme Pro–Drug Gene Therapy for Pancreatic Cancer In Vivo," *Surgery* 116:(2):205–213 (1994).

Dong et al., "In Vivo Replication–Deficient Adenovirus Vector–Mediated Transduction of the Cytosine Deaminase Gene Sensitizes Glioma Cells to 5–Fluorocytosine," *Human Gene Therapy* 7:713–720 (1996).

Goodman et al., "Adenoviral–Mediated Thymidine Kinase Gene Transfer into the Primate Brain Followed by Systemic Ganciclovir: Pathologic, Radiologic, and Molecular Studies," *Human Gene Therapy* 7:1241–1250 (1996).

Huber et al., "Retroviral–Mediated Gene Therapy for the Treatment of Hepatocellular Carcinoma: An Innovative Approach for Cancer Therapy," *Proc. Natl. Acad. Sci. USA* 88:8039–8043 (1991).

Ishii et al., "Mechanism of 'Bystander Effect' Killing in the Herpes Simplex Thymidine Kinase Gene–Modified Tumor System," *J. Cell Biochem.* Suppl. 18A, p. 226, Abstract DZ116 (1994).

Macri et al., "Delayed Morbidity and Mortality of Albumin/SV40 T–Antigen Transgenic Mice after Insertion of an α–Fetoprotein/Herpes Virus Thymidine Kinase Transgene and Treatment with Ganciclovir," *Human Gene Therapy* 5:175–182 (1994).

Manome et al., "Viral Vector Transduction of the Human Deoxycytidine Kinase cDNA Sensitizes Glioma Cells to the Cytotoxic Effects of Cytosine Arabinoside In Vitro and In Vivo," *Nature Medicine* 2(5):567–573 (1996).

Manome et al., "Gene Therapy for Malignant Gliomas Using Replication Incompetent Retroviral and Adenoviral Vectors Encoding the Cytochrome P450 2B1 Gene Together with Cyclophosphamide," *Gene Therapy* 3:513–520 (1996).

Markert et al., "Reduction and Elimination of Encephalitis in an Experimental Glioma Therapy Model with Attenuated Herpes Simplex Mutants that Retain Susceptibility to Acyclovir," *Neurosurgery* 32(4):597–603 (1993).

Martuza et al., "Experimental Therapy of Human Glioma by Means of a Genetically Engineered Virus Mutant," *Science* 252:854–856 (1991).

Okada et al., "Gene Therapy Against an Experimental Glioma Using Adeno–Associated Virus Vectors," *Gene Therapy* 3:957–964 (1996).

Perez–Cruet et al., "Adenovirus–Mediated Gene Therapy of Experimental Gliomas," *J. Neuroscience Research* 39:506–511 (1994).

Plautz et al., "Selective Elimination of Recombinant Genes In Vivo With a Suicide Retroviral Vector," *New Biologist* 3(7):709–715 (1991).

Qian et al., "Induction of Sensitivity to Ganciclovir in Human Hepatocellular Carcinoma Cells by Adenovirus–Mediated Gene Transfer of Herpes Simplex Virus Thymidine Kinase," *Hepatology* 22(1):118–123 (1995).

Ram et al., "The Effect of Thymidine Kinase Transduction and Ganciclovir Therapy on Tumor Vasculature and Growth of 9L Gliomas in Rats," *J. Neurosurg.* 81:256–260 (1994).

Shinoura et al., "Protein and Messenger RNA Expression of Connexin43 in Astrocytomas: Implications in Brain Tumor Gene Therapy," *J .Neurosurg.* 84:839–846 (1996).

Takamiya et al., "Gene Therapy of Malignant Brain Tumors: A Rat Glioma Line Bearing the Herpes Simplex Virus Type 1–Thymidine Kinase Gene and Wild Type Retrovirus Kills Other Tumor Cells," *J. Neuroscience Research* 33:493–503 (1992).

SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
         (A) LENGTH: 14 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:1:

GGCAGCTGCC TGCA                                                          14

(2) INFORMATION FOR SEQ ID NO:2:

(i) SEQUENCE CHARACTERISTICS:
         (A) LENGTH: 14 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:2:

GAAGGCGCGC CTTC                                                          14

(2) INFORMATION FOR SEQ ID NO:3:

(i) SEQUENCE CHARACTERISTICS:
         (A) LENGTH: 80 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:3:

GCGGCCGCAC GCGTACGTAC CGGTTCGAAG CGCGCACGGC CGACCATGGT TAACTCCGGA        60

CACGTGCGGA CCGCGGCCGC                                                    80

(2) INFORMATION FOR SEQ ID NO:4:

(i) SEQUENCE CHARACTERISTICS:
         (A) LENGTH: 28 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:4:

AAAATTCGAA CCTGGGGAGA AACCAGAG                                           28

(2) INFORMATION FOR SEQ ID NO:5:

(i) SEQUENCE CHARACTERISTICS:
         (A) LENGTH: 28 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:5:

GTTTCCCCGC GAATGGACAA GCTTAAAA                                28

(2) INFORMATION FOR SEQ ID NO:6:

(i) SEQUENCE CHARACTERISTICS:
        (A) LENGTH: 91 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

GCGGCCGCAC GCGTTGTTAA CAACCGGTTC GAAGCGCGCA GCGGCCGACC ATGGGTTTAA    60

ACTCCGGACC ACGTGCGGAC CGAGCGGCCG C                                  91

(2) INFORMATION FOR SEQ ID NO:7:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

AAAATTCGAA CAGGTAAGCG CCCCTTTG                                28

(2) INFORMATION FOR SEQ ID NO:8:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

GAGACCAAAG AGGGGTCCAA GCTTAAAA                                28

(2) INFORMATION FOR SEQ ID NO:9:

(i) SEQUENCE CHARACTERISTICS:
        (A) LENGTH: 101 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

GAGCTCAATC GATTGAATTC CCCGGGGATC CTCTAGAGTC GACCTGCAGC CACTGTGTTG    60

GATATCCAAC ACACTGGTAG GGATAACAGG GTAATCTCGA G                      101

(2) INFORMATION FOR SEQ ID NO:10:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

```
GGGGAGGCTA ACTGAGCGGG GATCCTCTAG AG                              32
```

(2) INFORMATION FOR SEQ ID NO:11:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

```
AAACACGATG ATAATATGGC CCTGTGGATC                                 30
```

ADENO-ASSOCIATED VIRUS VECTORS COMPRISING A FIRST AND SECOND NUCLEIC ACID SEQUENCE

CROSS-REFERENCE TO RELATED APPLICATION

This application is related to provisional patent application Ser. No. 60/013,209, filed Mar. 6, 1996, from which priority is claimed under 35 U.S.C. §119(e)(1) and which is incorporated herein by reference in its entirety.

TECHNICAL FIELD

The present invention relates generally to methods of treating solid tumors. More particularly, the invention relates to the use of recombinant adeno-associated virus (rAAV) virions to deliver a plurality of selected genes to cancerous cells and tissue. The method provides for the introduction of a drug-susceptibility gene and a second gene capable of providing an ancillary therapeutic effect into solid tumor cells. The invention also relates to rAAV virions that contain DNA useful in the treatment of neoplastic disease.

BACKGROUND OF THE INVENTION

Gene delivery is a promising method for the treatment of acquired and inherited diseases. A number of viral based systems for gene transfer purposes have been described, such as retroviral systems which are currently the most widely used viral vector systems for gene transfer. For descriptions of various retroviral systems, see, e.g., U.S. Pat. No. 5,219,740; Miller and Rosman (1989) BioTechniques 7:980–990; Miller, A. D. (1990) Human Gene Therapy 1:5–14; Scarpa et al. (1991) virology 180:849–852; Burns et al. (1993) Proc. Natl. Acad. Sci. USA 90:8033–8037; and Boris-Lawrie and Temin (1993) Cur. Opin. Genet. Develop. 3:102–109.

A number of adenovirus based gene delivery systems have also been developed. Human adenoviruses are double-stranded DNA viruses which enter cells by receptor-mediated endocytosis. These viruses are particularly well suited for gene transfer because they are easy to grow and manipulate and they exhibit a broad host range in vivo and in vitro. Adenovirus is easily produced at high titers and is stable so that it can be purified and stored. Even in the replication-competent form, adenoviruses generally cause only low level morbidity and are not associated with human malignancies. For descriptions of various adenovirus-based gene delivery systems, see, e.g., Haj-Ahmad and Graham (1986) J. Virol. 57:267–274; Bett et al. (1993) J. Virol. 67:5911–5921; Mittereder et al. (1994) Human Gene Therapy 5:717–729; Seth et al. (1994) J. Virol. 68:933–940; Barr et al. (1994) Gene Therapy 1:51–58; Berkner, K. L. (1988) BioTechniques 6:616–629; Rich et al. (1993) Human Gene Therapy 4:461–476.

The in vivo transfer of specific tumor suppressor genes, apoptotic genes, or genes that encode a particular toxic product to cancer cells, using such known gene delivery systems, will provide an attractive alternative to conventional avenues in the treatment of neoplastic disease. Such approaches are particularly indicated in the treatment of cancers that are refractive to conventional procedures such as surgery, radiotherapy and chemotherapy. In this regard, advances in molecular biology have identified a number of mechanisms that control cell growth and differentiation. Experimental treatments which specifically target these pathways using gene therapy are currently underway. Particularly, a number of approaches involving somatic gene therapy in cancer treatment have been investigated, including drug sensitization, genetic immunomodulation, normal tissue protection, gene replacement and antisense strategies. Gutierrez et al. (1992) Lancet 339:715–721, Anderson, W. F. (1994) Hum. Gene Ther. 5:1–2.

Of these approaches, drug sensitization has provided the most promising results to date. Drug sensitization involves the transfer of suicide genes (e.g., drug-susceptibility genes) to tumor cells to render those cells sensitive to compounds or compositions that are relatively nontoxic to normal cells. Moolten, F. L. (1994) Cancer Gene Ther. 1:279–287. Examples of suicide genes are thymidine kinase of herpes simplex virus (HSV-tk), cytochrome P450 (Manome et al. (1996) Gene Therapy 3:513–520), human deoxycytidine kinase (Manome et al. (1996) Nature Medicine 2(5):567–573) and the bacterial enzyme cytosine deaminase (Dong et al. (1996) Human Gene Therapy 7:713–720). Cells which express these genes are rendered sensitive to the effects of the relatively nontoxic prodrugs ganciclovir (HSV-tk), cyclophosphamide (cytochrome P450 2B1), cytosine arabinoside (human deoxycytidine kinase) or 5-fluorocytosine (bacterial cytosine deaminase). Culver et al. (1992) Science 256:1550–1552, Huber et al. (1994) Proc. Natl. Acad. Sci. USA 91:8302–8306.

The HSV-tk gene is the most widely studied drug-susceptibility gene. HSV-tk converts specific protoxic nucleoside analogues, such as acyclovir and ganciclovir, to monophosphate intermediates that are then phosphorylated by cellular kinases to provide potent DNA synthesis inhibitors. Cells capable of expressing HSV-tk are rendered extremely sensitive to the toxic effect of ganciclovir, whereas non-HSV-tk expressing cells are much less sensitive, resulting in a large therapeutic index. Tumor modeling experiments using gene delivery of HSV-tk have demonstrated complete regression of established tumors and long-term animal survival, even though only a portion of the tumor cells were actually transduced with the HSV-tk gene. This so-called "bystander" cytocidal effect provides an important therapeutic advantage, as it avoids the need to transduce 100% of the tumor cells with the HSV-tk gene. For a detailed description of the bystander effect, see, e.g., Vrionis et al. (1995) J. Neurosurg. 83:698–704, Ishii et al. (1994) J. Cell Biochem. 18A:226, and Freeman et al. (1993) Cancer Res. 53:5274–5283.

In vivo transfer of drug-susceptibility genes is especially suited for treating solid tumors that are growing rapidly and invading normal tissue composed largely of nonproliferating or quiescent cells. Such therapies have thus been applied to the treatment of hepatocellular carcinoma (HCC). HCC is a common human malignancy that is particularly refractive to conventional cancer therapies. Modifications in conventional chemotherapeutic protocols, such as intrahepatic artery infusion of cytotoxic drugs, are able to improve tumor responses but fail to substantially improve patient prognosis or survival. Venook, A. P. (1994) J. Clin. Oncol. 12:1323–1334, Farmer et al. (1994) Cancer 73:2669–2670. The most effective approach to date in the treatment of HCC entails complete surgical ablation of the tumor by partial hepatectomy or by total hepatectomy coupled with liver transplantation.

Recently, investigators have shown suppression of tumor growth and increased survival rates in transgenic murine subjects that express HSV-tk in HCC cells when those subjects were treated with ganciclovir. Macri et al. (1994) Hum. Gene Ther. 5:175–182. Retroviral vehicles have been used to transfer varicella-zoster virus thymidine kinase into HCC tumor cells to confer sensitivity to 6-methoxypurine arabino-nucleoside. Huber et al. (1991) *Proc. Natl. Acad. Sci. USA* 88:8039–8043. Further, adenoviral vehicles have been used to transfer HSV-tk into HCC cells to confer sensitivity to ganciclovir. Qian et al. (1995) *Hepatology* 22:118–123.

The use of replication-deficient retroviral vectors to transduce the HSV-tk gene into solid tumor cells is also being clinically investigated as a new approach in the treatment of human ovarian cancer. Ishii et al. (1994) *J. Cell Biochem.* 18A:226. Additionally, studies have been described wherein pancreatic cancer xenografts were successfully treated in severe combined immunodeficient (scid) mice using retrovirally-mediated HSV-tk transduction and ganciclovir treatment. DiMaio et al. (1994) *Surgery* 116:205–213. Retroviral vectors have also been used to transduce lymphoma, fibrosarcoma and adenocarcinoma cells with the HSV-tk gene in culture and in vivo, rendering those cells conditionally sensitive to ganciclovir. Plautz et al. (1991) *New Biol.* 3:709–715, Freeman et al. (1991) *Federal Register* 56 #138, p. 33174, Moolten et al. (1990) *Hum. Gene Ther.* 1:125–134, Moolten, F. L. (1986) *Cancer Res.* 46:5276–5281.

Drug sensitivity therapies are also being investigated in the treatment of malignant melanoma. The incidence of malignant melanoma in the United States continues to increase at a rate of about 2–3% annually, resulting in increased morbidity and mortality as a result of this disease. This serious health problem is even further exacerbated, as an effective treatment for melanoma has remained elusive due to a high propensity for metastatic spread and the resistance of such tumor cells to the most widely used chemotherapeutic regimes. Accordingly, new alternative therapies in the treatment of malignant melanoma include sensitizing melanoma cells to ganciclovir by transducing those cells with HSV-tk via an adenoviral-based gene delivery system. Bonnekoh et al. (1995) *J. Investigative Dermatology* 104:313–317.

A great deal of interest has also developed around providing alternative therapeutic techniques for the treatment of malignant brain tumors. Brain tumors, e.g., malignant primary intracranial tumors or metastatic tumors, are rapidly debilitating and extremely lethal forms of cancer. The most common primary intracranial tumors are malignant gliomas which account for about 30–40% of primary brain tumors in adults. Patients presenting with glioblastoma multiforme, a highly malignant form of glioma, have an average life expectancy of less than about one year despite a number of recent improvements in neurosurgical techniques and neuroradiological imaging modalities. In light of this poor prognosis, and the inability of current therapeutic approaches (e.g., surgical resection, irradiation and chemotherapy) to effectively treat malignant gliomas, drug sensitization therapy, such as the in vivo transduction of glioma cells with HSV-tk, may provide a new therapeutic approach in the treatment of intracranial solid tumors.

In particular, several methods have been developed for transducing glioma cells with HSV-tk. One method involves in situ inoculation of a brain tumor mass with packaging cells capable of producing replication-defective retroviral particles carrying the HSV-tk gene, followed by treatment with ganciclovir. Ram et al. (1994) *J. Neurosurg.* 81:256–260, Culver et al. (1992) *Science* 256:1550–1552, Kim et al. (1991) *J. Neurosurg.* 74:27–37, Short et al. (1990) *J. Neurosci. Res.* 27:427–439. The retroviral particles are secreted from the inoculated packaging cells to transduce local tumor cells, rendering them sensitive to the ganciclovir pro-drug. Another approach involves intra-tumoral injection with recombinant adenovirus vectors to transduce malignant glioma cells with HSV-tk, coupled with ganciclovir treatment. Badie et al. (1994) *Neurosurgery* 35:910–916, Chen et al. (1994) *Proc. Natl. Acad. Sci. USA* 91:3054–3057, Perez-Cruet et al. (1994) *J. Neurosci Res.* 39:506–511. Yet another method involves intra-tumoral injection of genetically engineered herpes simplex virus (HSV) particles into solid brain tumors. Chambers et al. (1995) *Proc. Natl. Acad. Sci. USA* 92:1411–1415, Markert et al. (1993) *Neurosurgery* 32:597–603, Takamiya et al. (1993) *J. Neurosurg.* 79:104–10, Martuza et al. (1991) *Science* 252:854–856.

Although drug sensitization techniques, such as the above-described HSV-tk transduction therapies, have shown promise in the treatment of cancer, such approaches have not yet fulfilled their theoretical potential. This shortcoming may be due in part to the low transduction efficiency of retroviral vectors. Furthermore, the pathogenicity of retroviral and adenoviral particles limits the use of such particles in developing safe and effective gene delivery systems for use in human subjects.

The shortcomings of prior retroviral and adenoviral-based suicide gene delivery systems could be overcome in part by developing vectors that provide an ancillary therapeutic effect in conjunction with drug sensitization. In this regard, gene transfer systems could be used to also increase the immunogenicity of transduced tumor cells, leading to a local and/or systemic antitumor effect that is not dependent on the administration of a chemotherapeutic agent. The immunogenicity of the transduced cells could be increased using gene transfer to cause local cytokine production or enhance the expression of major histocompatibility complex antigen expression. Gansbacher et al. (1990) *Cancer Res.* 50:7820, Tepper et al. (1989) *Cell* 57:503, Itaya et al. (1987) *Cancer Res.* 47:3136. Alternatively, gene transfer systems could be used to transduce tumor cells with tumor suppressor genes, alone or in conjunction with a drug-sensitizing gene or a cytokine gene. Despite the advantages of such systems, gene delivery systems that combine multiple antitumor strategies in a single gene delivery vector have not heretofore been described.

Further, limitations due to pathogenic or immunogenic characteristics of the adenoviral or retroviral vectors could be avoided by using an alternative gene delivery system. In this regard, even though retroviral vectors are able to mediate stable, integrated gene transfer in actively dividing cells which provides for enhanced selectivity in the context of treating some neoplastic disease (Miller et al. (1990) *Mol. Cell Biol.* 10:4239–4242), these systems suffer from several serious drawbacks. For example, the inability to transduce non-dividing or slowly-dividing cells lowers the ability of such systems to treat solid tumors where only a portion of the cells are proliferating at one time. Replication-incompetent retroviral gene delivery systems are also known to be inefficient at gene transfer, often failing to transduce cells at distances of more than a few millimeters from an injection site. The use of retroviral particles in gene delivery is also hampered by the inability to produce substantial viral titers.

The use of adenoviral vectors in gene delivery avoids a number of the problems associated with retroviral-based systems. Adenoviruses can be produced in high titers, and are able to infect quiescent as well as replicating target cells. Despite these advantages, adenovirus vector systems still have several drawbacks which limit their effectiveness in gene delivery. Most significantly, high dose intracerebral injection of adenoviral vectors alone has been shown to produce a direct cytotoxic (neurotoxic) effect, and synergistic toxicity has been observed when such injections are coupled with ganciclovir (GCV) administration. Goodman et al. (1996) *Hum Gene Therapy* 7:1241–1250. These results compel caution in the clinical use of recombinant adenovirus. Adenovirus vectors also express viral proteins that may elicit a strong non-specific immune response in the host. This non-specific immune reaction may increase toxicity or preclude subsequent treatments because of humoral and/or T cell responses against the adenoviral particles.

Thus, there remains a need to provide an alternative approach of sensitizing solid tumor cells using a gene delivery method that avoids the problems associated with prior retroviral and adenoviral vector-based systems. The method should also be capable of providing an ancillary therapeutic effect to increase the efficacy of the therapeutic method. An ancillary therapeutic effect could be provided by increasing the immune recognition of a transduced tumor cell by the host immune cells. Alternatively, an ancillary effect could be effected using tumor suppressor genes to provide a cytostatic effect in the transduced tumor cells. One particularly attractive alternative would entail the use of adeno-associated virus (AAV) gene delivery systems.

Recombinant vectors based on AAV particles have been used for DNA delivery. AAV is a helper-dependent DNA parvovirus which belongs to the genus Dependovirus. AAV has a wide host range and is able to replicate in cells from any species so long as there is also a successful infection of such cells with a suitable helper virus. AAV has not been associated with any human or animal disease. For a review of AAV, see, e.g., Berns and Bohenzky (1987) *Advances in Virus Research* (Academic Press, Inc.) 32:243–307.

The construction of recombinant vectors based on AAV has been described. See, e.g., U.S. Pat. Nos. 5,173,414 and 5,139,941; International Publication Numbers WO 92/01070 (published Jan. 23, 1992) and WO 93/03769 (published Mar. 4, 1993); Lebkowski et al. (1988) *Molec. Cell. Biol.* 8:3988–3996; Vincent et al. (1990) *Vaccines 90* (Cold Spring Harbor Laboratory Press); Carter, B. J. (1992) *Current Opinion in Biotechnology* 3:533–539; Muzyczka, N. (1992) *Current Topics in Microbiol. and Immunol.* 158:97–129; and Kotin, R. M. (1994) *Human Gene Therapy* 5:793–801.

Recombinant AAV vectors are capable of transducing several cell types, including hematopoietic cells, respiratory epithelial cells (Flotte et al. (1992) *Am. J. Respir. Cell Mol. Biol.* 7:349–356; Flotte et al. (1993) *J. Biol. Chem.* 268:3781–3790; Flotte et al. (1993) *Proc. Natl. Acad. Sci. USA* 90:10613–10617) and neurons of the central nervous system (Kaplitt et al. (1994) *Nature Genetics* 8:148–154). These cell types are well-differentiated, slowly-dividing or postmitotic. Flotte et al. (1993) *Proc. Natl. Acad. Sci. USA* 90:10613–10617; Kaplitt et al. (1994) *Nature Genetics* 8:148–154.

A recombinant AAV-based gene transfer system has been described for the transduction of HSV-tk into cells of the central or peripheral nervous systems in a mammalian subject to render those cells sensitive to ganciclovir. See, International Publication No. WO 95/28493. This system is particularly designed for use in the treatment of neurological disorders such as Parkinson's disease and in the treatment of brain tumors. Even though this system may avoid problems associated with prior adenoviral or retroviral-based systems, it fails to provide an ancillary therapeutic effect, thereby reducing its overall effectiveness.

Accordingly, there remains a need to provide an AAV-based gene delivery system that is capable of transducing a wide range of solid cancer cells to render them sensitive to selected compounds or compositions, wherein the system also provides an ancillary therapeutic effect. Particularly, there remains a need to provide a multi-faceted delivery system that increases the immune recognition of a transduced tumor cell by the host immune cells in conjunction with providing drug susceptibility. There also remains a need to provide a system which provides a cytostatic effect in a transduced, drug-susceptible tumor cell.

SUMMARY OF THE INVENTION

It is a primary object of the present invention to provide an AAV-based gene delivery system for transducing solid cancer cells with a drug sensitizing gene, wherein the system also provides for an ancillary therapeutic effect. The system is capable of being used to transduce a wide range of different tumor cell types, and is thus useful in the treatment of a variety of neoplastic diseases. The ancillary therapeutic effect serves to increase the overall efficacy of the present therapeutic system, and is provided by either increasing a local immune response to transduced tumor cells by the host immune cells or, imparting a cytostatic and/or cytotoxic effect to the transduced cell. The underlying AAV particles avoid a number of the problems encountered with prior retroviral-or adenoviral-based gene delivery systems.

Accordingly, in one embodiment, the invention relates to a method of simultaneously delivering a first gene and a second gene to a target solid tumor cell (i.e., transducing the target cell). Particularly, a recombinant adeno-associated virus (rAAV) virion is provided which includes a first gene that is capable of being expressed to provide a transduced target cell with enhanced susceptibility to a selected cytotoxic agent. The rAAV virion also includes a second gene that is capable of providing an ancillary therapeutic effect to the transduced cell. The first gene and the second gene are operably linked to control elements that are capable of directing the in vivo transcription and translation of those genes in the transduced cell. Each gene may be associated with a discrete set of control elements, or both genes can be associated with a single group of control elements.

In one aspect of the invention, the second gene is capable of being expressed by the transduced tumor cell to enhance the immunogenicity of the transduced cell. Thus, the second gene can encode a cytokine, such as type I interferons, tumor necrosis factor (TNF), interleukin-2 (IL-2), gamma interferon (IFN-γ), lymphotoxin, interleukin-12 (IL-12) and granulocyte-macrophage colony-stimulating factor (GM-CSF). Alternatively, the second gene is capable of being expressed to provide a tumorstatic effect in the transduced cell. In this regard, the second gene can be a tumor suppressor gene, such as p53, RB1, WT1, NF1, VHL, and APC.

In another embodiment of the invention, a method is provided for treating neoplastic disease in a mammalian subject. The method entails the steps of: (1) transducing a solid tumor cell of a mammalian subject in vivo using a therapeutically effective amount of a pharmaceutical composition which comprises (a) a pharmaceutically acceptable excipient, and (b) rAAV virions, where the rAAV virions comprise an AAV vector that includes a first gene that is capable of being expressed to provide the transduced tumor cell with enhanced susceptibility to a selected cytotoxic agent, a second gene that is capable of providing an ancillary therapeutic effect, and control elements operably linked to the first gene and the second gene such that the control elements are capable of directing the in vivo transcription and translation of the first gene and the second gene when they are present in the mammalian subject; and then (2) administering a therapeutically effective amount of the selected cytotoxic agent to the mammalian subject.

As described above, the second gene of the rAAV virion can be used to enhance the immunogenicity of the transduced cell or to provide a tumorstatic effect in the transduced cell. Thus, the second gene can encode a cytokine (e.g., alpha interferon (IFN-α), beta interferon (IFN-β), gamma interferon (IFN-γ), tumor necrosis factor (TNF), interleukin-2 (IL-2), lymphotoxin, interleukin-12 (IL-12) and granulocyte-macrophage colony-stimulating factor (GM-CSF)), or the second gene can be a tumor suppressor gene (e.g., p53, RB1, WT1, NF1, VHL, and APC).

In other embodiments, the invention is directed to the provision of an AAV vector which includes a drug susceptibility gene and a second gene, wherein the second gene either encodes a cytokine or is a tumor suppressor gene. The first gene and the second gene are operably linked to control elements capable of directing the in vivo transcription and translation thereof. The invention is also directed to a recombinant AAV virion containing the subject vector.

In yet another embodiment of the invention, AAV vectors are provided which include a single gene, such as an interferon gene or a tumor suppressor gene. The AAV vectors can be used to provide either an immunogenic or a tumorstatic effect in a transduced solid tumor cell.

These and other embodiments of the invention will readily occur to those of ordinary skill in the art in view of the disclosure herein.

DETAILED DESCRIPTION OF THE INVENTION

Figure 1A:
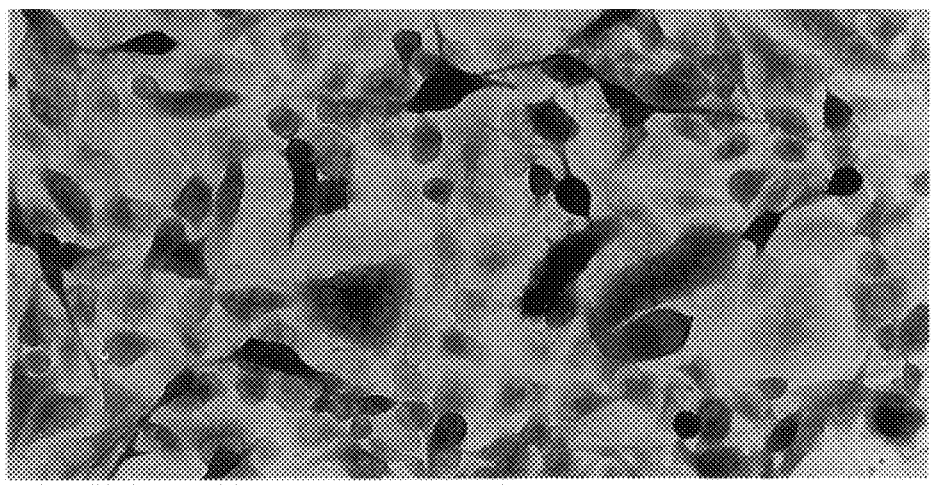
FIG. 1 depicts the in vitro transduction efficiency of the rAAVLacZ virion in human U-251SP glioma cells as described in Example 1. Cultured U-251SP cells were transduced with recombinant AAVLacZ virion and incubated for 12 hours as monolayers, the medium was changed, and the cells incubated for an additional 36 hours after which the cells were stained for β-galactosidase activity with X-Gal. The cells in part (A) were transduced with the recombinant virions at a multiplicity of infection (MOI) of $3 \times 10^5$, cells in part (B) at a MOI of $3 \times 10^4$, and the cells in part (C) at a MOI of $3 \times 10^3$. The cells in part (F) were not transduced (MOI of 0) and thus formed a control. The cells in part (D) and (E) were transduced at a MOI of $3 \times 10^5$, and incubated in fresh medium for 7 days or 42 days, respectively, before staining with X-Gal. For purposes of the present invention, a particular MOI value represents the number of viral particles per cell in a sample. The number of viral particles present in a cell sample can be ascertained using the dot-blot assay described below to obtain a value representative of the number of viral genomes present in a particular sample. In this regard, it is assumed herein that each genome is equivalent to a single viral particle. In each of parts (A)–(F), darkly stained cells indicate those successfully transduced with the rAAVLacZ virion (original magnification of ×20).
Figure 1B:
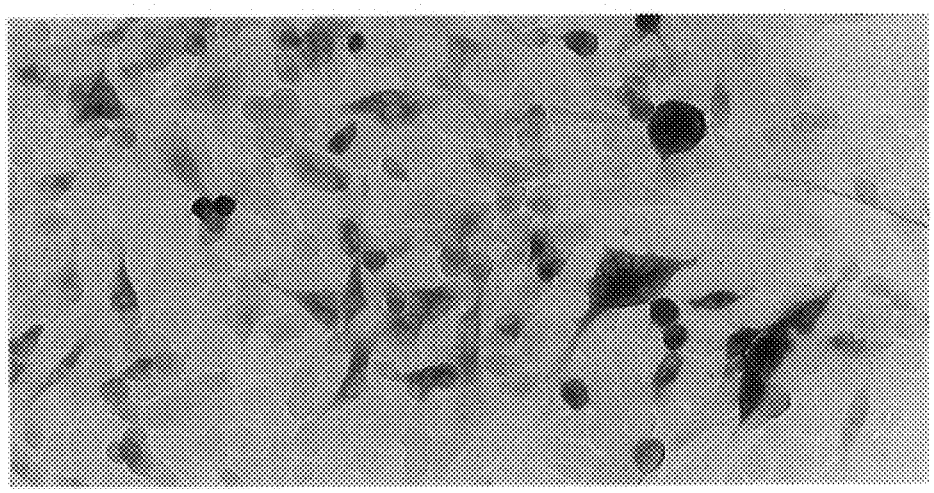
Figure 1C:
Figure 1D:
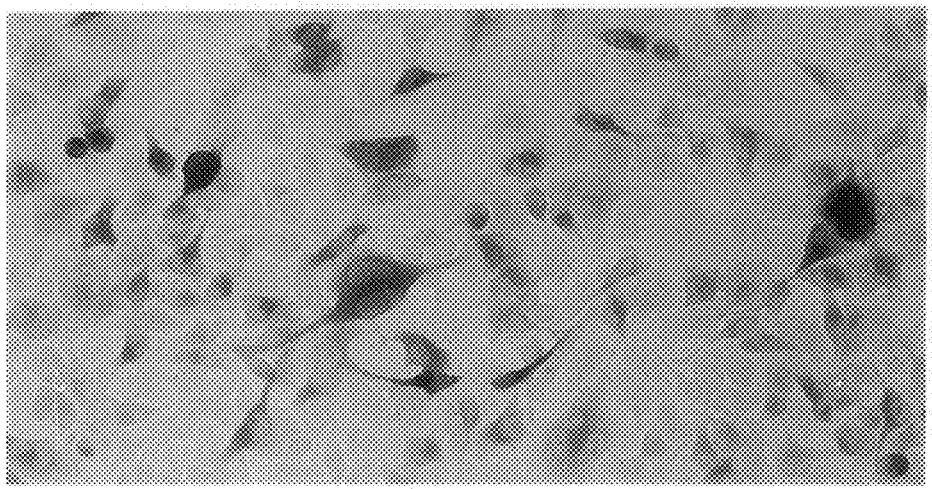
Figure 1E:
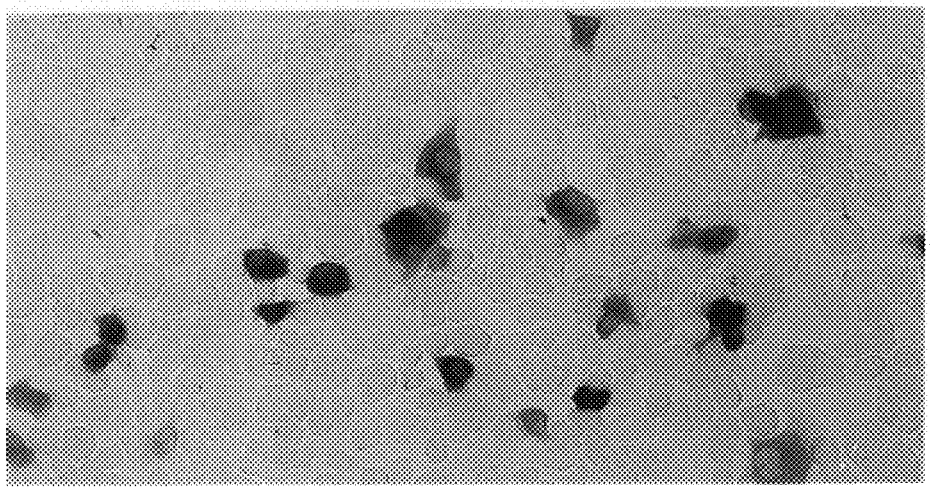
Figure 1F:
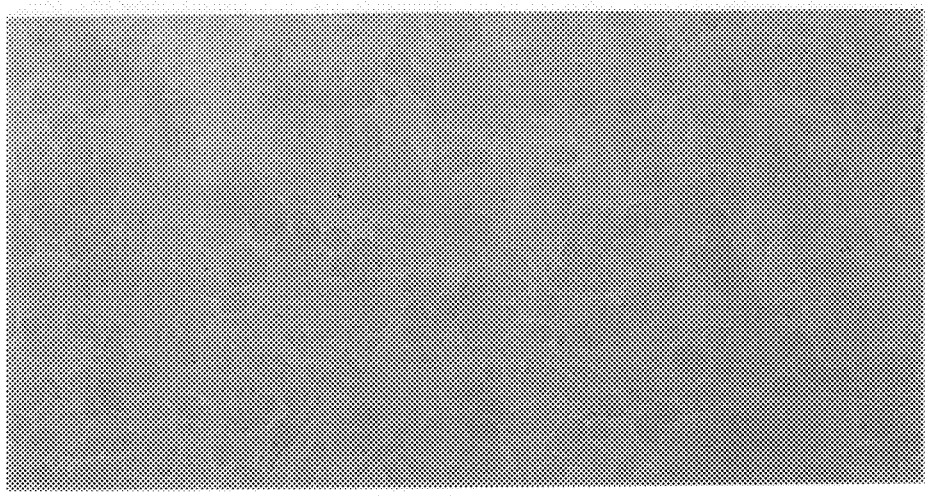

The practice of the present invention will employ, unless otherwise indicated, conventional methods of virology, microbiology, molecular biology and recombinant DNA techniques within the skill of the art. Such techniques are explained fully in the literature. See, e.g., Sambrook, et al. *Molecular Cloning: A Laboratory Manual* (Current Edition); *DNA Cloning: A Practical Approach*, vol. I & II (D. Glover, ed.); *Oligonucleotide Synthesis* (N. Gait, ed., Current Edition); *Nucleic Acid Hybridization* (B. Hames & S. Higgins, eds., Current Edition); *Transcription and Translation* (B. Hames & S. Higgins, eds., Current Edition); *CRC Handbook of Parvoviruses*, vol. I & II (P. Tijessen, ed.); *Fundamental Virology*, 2nd Edition, vol. I & II (B. N. Fields and D. M. Knipe, eds.)

All publications, patents and patent applications cited herein, whether supra or infra, are hereby incorporated by reference in their entirety.

As used in this specification and the appended claims, the singular forms "a," "an" and "the" include plural references unless the content clearly dictates otherwise.

A. Definitions

In describing the present invention, the following terms will be employed, and are intended to be defined as indicated below.

"Gene transfer" or "gene delivery" refers to methods or systems for reliably inserting foreign DNA into host cells.

Such methods can result in transient expression of non-integrated transferred DNA, extrachromosomal replication and expression of transferred replicons (e.g., episomes), or integration of transferred genetic material into the genomic DNA of host cells. Gene transfer provides a unique approach for the treatment of acquired and inherited diseases. A number of systems have been developed for gene transfer into mammalian cells. See, e.g., U.S. Pat. No. 5,399,346.

By "vector" is meant any genetic element, such as a plasmid, phage, transposon, cosmid, chromosome, virus, virion, etc., which is capable of replication when associated with the proper control elements and which can transfer gene sequences between cells. Thus, the term includes cloning and expression vehicles, as well as viral vectors.

By "AAV vector" is meant a vector derived from an adeno-associated virus serotype, including without limitation, AAV-1, AAV-2, AAV-3, AAV-4, AAV-5, AAVX7, etc. AAV vectors can have one or more of the AAV wild-type genes deleted in whole or part, preferably the rep and/or cap genes (described below), but retain functional flanking ITR sequences (also described below). Functional ITR sequences are necessary for the rescue, replication and packaging of the AAV virion. Thus, an AAV vector is defined herein to include at least those sequences required in cis for replication and packaging (e.g., functional ITRs) of the virus. The ITRs need not be the wild-type nucleotide sequences, and may be altered, e.g., by the insertion, deletion or substitution of nucleotides, so long as the sequences provide for functional rescue, replication and packaging.

By "recombinant virus" is meant a virus that has been genetically altered, e.g., by the addition or insertion of a heterologous nucleic acid construct into the particle.

By "AAV virion" is meant a complete virus particle, such as a wild-type (wt) AAV virus particle (comprising a linear, single-stranded AAV nucleic acid genome associated with an AAV capsid protein coat). In this regard, single-stranded AAV nucleic acid molecules of either complementary sense, e.g., "sense" or "antisense" strands, can be packaged into any one AAV virion and both strands are equally infectious.

A "recombinant AAV virion," or "rAAV virion" is defined herein as an infectious, replication-defective virus composed of an AAV protein shell, encapsidating a heterologous DNA molecule of interest which is flanked on both sides by AAV ITRs. A rAAV virion is produced in a suitable host cell which has had an AAV vector, AAV helper functions and accessory functions introduced therein. In this manner, the host cell is rendered capable of encoding AAV polypeptides that are required for packaging the AAV vector (containing a recombinant nucleotide sequence of interest) into recombinant virion particles for subsequent gene delivery.

The term "transfection" is used to refer to the uptake of foreign DNA by a cell. A cell has been "transfected" when exogenous DNA has been introduced inside the cell membrane. A number of transfection techniques are generally known in the art. See, e.g., Graham et al. (1973) *Virology*, 52:456, Sambrook et al. (1989) *Molecular Cloning*, a laboratory manual, Cold Spring Harbor Laboratories, New York, Davis et al. (1986) *Basic Methods in Molecular Biology*, Elsevier, and Chu et al. (1981) *Gene* 13:197. Such techniques can be used to introduce one or more exogenous DNA moieties, such as a plasmid vector and other nucleic acid molecules, into suitable host cells. The term refers to both stable and transient uptake of the genetic material.

The term "transduction" denotes the delivery of a DNA molecule to a recipient cell either in vivo or in vitro, via a replication-defective viral vector, such as via a recombinant AAV virion.

The term "cytokine" encompasses the family of protein mediators of both natural and acquired immunity. In general, cytokines are synthesized in response to inflammatory or antigenic stimuli and act locally, in an autocrine or paracrine fashion, by binding to certain high affinity receptors on target cells. Cytokines are usually classified into four groups according to their principal actions. The first group includes those cytokines that mediate natural immunity, such as type I interferons (e.g., $\alpha$- and $\beta$-interferon) and the pro-inflammatory cytokines (e.g., tumor necrosis factor, interleukin-1, interleukin-6, and the family of chemokines). The predominate source of these molecules is mononuclear phagocytes. The second group of cytokines are derived largely from antigen-stimulated $CD4^+$ T lymphocytes, and serve to regulate the activation, growth, and differentiation of B and T cells. Exemplary molecules from this group include interleukin-2, interleukin-4, and transforming growth factor-$\beta$. The third general group of cytokines are produced by antigen-activated CD4+ and CD8+ T lymphocytes. Exemplary members of this group include interferon-$\gamma$, lymphotoxin, interleukin-10, interleukin-5 and interleukin-12. The fourth group of cytokines are collectively referred to as colony-stimulating factors and include molecules derived from marrow stromal cells and T cells. Exemplary molecules include granulocyte-macrophage colony stimulating factor, interleukin-3 and interleukin-7.

The term "heterologous" as it relates to nucleic acid sequences such as gene sequences and control sequences, denotes sequences that are not normally joined together, and/or are not normally associated with a particular cell. Thus, a "heterologous" region of a nucleic acid construct or a vector is a segment of nucleic acid within or attached to another nucleic acid molecule that is not found in association with the other molecule in nature. For example, a heterologous region of a nucleic acid construct could include a coding sequence flanked by sequences not found in association with the coding sequence in nature. Another example of a heterologous coding sequence is a construct where the coding sequence itself is not found in nature (e.g., synthetic sequences having codons different from the native gene). Similarly, a cell transformed with a construct which is not normally present in the cell would be considered heterologous for purposes of this invention. Allelic variation or naturally occurring mutational events do not give rise to heterologous DNA, as used herein.

By "DNA" is meant a polymeric form of deoxyribonucleotides (adenine, guanine, thymine, or cytosine) in double-stranded or single-stranded form, either relaxed and supercoiled. This term refers only to the primary and secondary structure of the molecule, and does not limit it to any particular tertiary forms. Thus, this term includes single- and double-stranded DNA found, inter alia, in linear DNA molecules (e.g., restriction fragments), viruses, plasmids, and chromosomes. In discussing the structure of particular DNA molecules, sequences may be described herein according to the normal convention of giving only the sequence in the 5' to 3' direction along the nontranscribed strand of DNA (i.e., the strand having the sequence homologous to the mRNA). The term captures molecules that include the four bases adenine, guanine, thymine, or cytosine, as well as molecules that include base analogues which are known in the art.

A "gene" or "coding sequence" or a sequence which "encodes" a particular protein, is a nucleic acid molecule which is transcribed (in the case of DNA) and translated (in the case of mRNA) into a polypeptide in vitro or in vivo when placed under the control of appropriate regulatory sequences. The boundaries of the gene are determined by a start codon at the 5' (amino) terminus and a translation stop codon at the 3' (carboxy) terminus. A gene can include, but is not limited to, cDNA from prokaryotic or eukaryotic mRNA, genomic DNA sequences from prokaryotic or eukaryotic DNA, and even synthetic DNA sequences. A transcription termination sequence will usually be located 3' to the gene sequence.

The term "control elements" refers collectively to promoter regions, polyadenylation signals, transcription termination sequences, upstream regulatory domains, origins of replication, internal ribosome entry sites ("IRES"), enhancers, and the like, which collectively provide for the replication, transcription and translation of a coding sequence in a recipient cell. Not all of these control elements need always be present so long as the selected coding sequence is capable of being replicated, transcribed and translated in an appropriate host cell.

The term "promoter region" is used herein in its ordinary sense to refer to a nucleotide region comprising a DNA regulatory sequence, wherein the regulatory sequence is derived from a gene which is capable of binding RNA polymerase and initiating transcription of a downstream (3'-direction) coding sequence.

"Operably linked" refers to an arrangement of elements wherein the components so described are configured so as to perform their usual function. Thus, control elements operably linked to a coding sequence are capable of effecting the expression of the coding sequence. The control elements need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

For the purpose of describing the relative position of nucleotide sequences in a particular nucleic acid molecule throughout the instant application, such as when a particular nucleotide sequence is described as being situated "upstream," "downstream," "5'," or "3+" relative to another sequence, it is to be understood that it is the position of the sequences in the non-transcribed strand of a DNA molecule that is being referred to as is conventional in the art.

"Homology" refers to the percent of identity between two polynucleotide or two polypeptide moieties. The correspondence between the sequence from one moiety to another can be determined by techniques known in the art. For example, homology can be determined by a direct comparison of the sequence information between two polypeptide molecules by aligning the sequence information and using readily available computer programs. Alternatively, homology can be determined by hybridization of polynucleotides under conditions which form stable duplexes between homologous regions, followed by digestion with single-stranded-specific nuclease(s), and size determination of the digested fragments. Two DNA, or two polypeptide sequences are "substantially homologous" to each other when at least about 80%, preferably at least about 90%, and most preferably at least about 95% of the nucleotides or amino acids match over a defined length of the molecules, as determined using the methods above.

By "isolated" when referring to a nucleotide sequence, is meant that the indicated molecule is present in the substantial absence of other biological macromolecules of the same type. Thus, an "isolated nucleic acid molecule which encodes a particular polypeptide" refers to a nucleic acid molecule which is substantially free of other nucleic acid molecules that do not encode the subject polypeptide; however, the molecule may include some additional bases or moieties which do not deleteriously affect the basic characteristics of the composition.

By "mammalian subject" is meant any member of the class Mammalia including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be covered.

B. General Methods

The present invention provides for the successful transfer of a first gene into a solid tumor cell using recombinant AAV virions, wherein the first gene, when expressed, renders the transduced cell sensitive to a selected cytotoxic compound or composition. The method allows for the direct, in vivo injection of recombinant AAV virions into tumor cell masses, e.g., by intra-tumoral injection. The invention also provides for the simultaneous delivery of a second gene using the recombinant AAV virions, wherein the second gene is capable of providing an ancillary therapeutic effect when expressed within the transduced cell.

The recombinant AAV virions of the present invention, including the DNA of interest, can be produced using standard methodology, known to those of skill in the art. The methods generally involve the steps of (1) introducing an AAV vector into a host cell; (2) introducing an AAV helper construct into the host cell, where the helper construct includes AAV coding regions capable of being expressed in the host cell to complement AAV helper functions missing from the AAV vector; (3) introducing one or more helper viruses and/or accessory function vectors into the host cell, wherein the helper virus and/or accessory function vectors provide accessory functions capable of supporting efficient recombinant AAV ("rAAV") virion production in the host cell; and (4) culturing the host cell to produce rAAV virions. The AAV vector, AAV helper construct and the helper virus or accessory function vector(s) can be introduced into the host cell either simultaneously or serially, using standard transfection techniques.

1. AAV Vectors

AAV vectors are constructed using known techniques to at least provide, as operatively linked components in the direction of transcription, (a) control elements including a transcriptional initiation region, (b) the DNA of interest, and (c) a transcriptional termination region. The control elements are selected to be functional in the targeted tumor cell. The resulting construct which contains the operatively linked components is bounded (5' and 3') with functional AAV ITR sequences.

The nucleotide sequences of AAV ITR regions are known. See, e.g., Kotin, R. M. (1994) *Human Gene Therapy* 5:793–801; Berns, K. I. "Parvoviridae and their Replication" in *Fundamental Virology*, 2nd Edition, (B. N. Fields and D. M. Knipe, eds.) for the AAV-2 sequence. AAV ITRs used in the vectors of the invention need not have a wild-type nucleotide sequence, and may be altered, e.g., by the insertion, deletion or substitution of nucleotides. Additionally, AAV ITRs may be derived from any of several AAV serotypes, including without limitation, AAV-1, AAV-2, AAV-3, AAV-4, AAV-5, AAVX7, etc. Furthermore, 5' and 3' ITRs which flank a selected nucleotide sequence in an AAV expression vector need not notnecessarily be identical or derived from the same AAV serotype or isolate, so long as they function as intended, i.e., to allow for excision and replication of the bounded nucleotide sequence of interest when AAV rep gene products are present in the cell.

Suitable DNA molecules for use in AAV vectors will generally be less than about 5 kilobases (kb) in size and will include, for example, a first gene that encodes a protein that provides sensitivity to a selected compound or composition, and a second gene that is capable of providing an ancillary therapeutic effect, such as wherein the second gene encodes a protein having a desired immunogenic effect, or wherein the second gene is capable of providing a tumorstatic effect.

More particularly, the first gene will be a drug-susceptibility gene such as the herpes simplex virus thymidine kinase (HSV-tk) gene, a cytochrome P450 2B1 gene (Manome et al. (1996) *Gene Therapy* 3:513–520), a human deoxycytidine kinase gene (Manome et al. (1996) *Nature Medicine* 2(5):567–573), or the *Eschericia coli* (*E. coli*) cytosine deaminase gene (Dong et al. (1996) *Human Gene Therapy* 7:713–720). The HSV-tk gene has been previously mapped, cloned and sequenced, and is readily available (EMBL HEHSV1TK, Accession X03764, EMBL HEHS07, Accession V00466). The HSV-tk gene can be obtained from natural sources, such as from the viral genome of Herpes simplex virus type I (HSV-1) or from the Herpes simplex virus type II (HSV-2) genome. The varicella zoster virus (VZV) genome also includes a specific thymidine kinase gene (VZV-tk) which has been cloned, sequenced and characterized (Mori et al. (1988) *Intervirology* 29:301–310, (1986) *J. Gen. Virol.* 67:1759–1816). Thus, the VZV-tk gene can be obtained from the VZV genome. The drug-susceptibility gene can also be obtained from known recombinant sources, for example, from the G1TkSvNa.53 retroviral vector (Culver et al. (1994) *Hum. Gene Ther.* 5:343–379) which contains a HSV-1 thymidine kinase (HSV-tk) gene cDNA, or from plasmid HSBV-106 (available from Gibco, Gaithersburg, Md.) which also contains the HSV-tk gene. Alternatively, HSV-tk or VZV-tk oligonucleotides can be synthetically derived, using a combination of solid phase direct oligonucleotide synthesis chemistry and enzymatic ligation methods which are conventional in the art. Synthetic sequences can be prepared using commercially available oligonucleotide synthesis devices such as those devices available from Applied Biosystems, Inc. (Foster City, Calif.).

The *E. coli* cytosine deaminase gene has also been cloned and sequenced (Danielson et al. (1992) *Mol. Microbiol.* 6:1335–1344, Austin et al. (1993) *Mol. Pharmacol.* 43:380–387, Dong et al. (1996) *Human Gene Therapy* 7:713–720), and the gene sequence has been deposited with GenBank under Accession No. S56903. The *E. coli* cytosine deaminase gene can therefore also be obtained from a number natural or synthetic sources known to those skilled in the art.

The human deoxycytidine kinase (dCK) gene has been cloned, and a cDNA encoding dCK has been expressed (Chottiner et al. (1991) *Proc. Natl. Acad. Sci. USA* 88:1531–1535, Manome et al. (1996) *Nature Medicine* 2(5):567–573). A rat cytochrome P450 2B1 cDNA has also been cloned (Manome et al. (1996) *Gene Therapy* 3:513–520). Thus, these genes can also be readily obtained.

The second gene is selected to provide an ancillary therapeutic effect to a tumor cell that has been transduced with the drug-sensitizing gene. For example, the second gene can enhance the immunogenicity of the transduced tumor cell. In this regard, several studies have indicated that the weak immunogenicity of certain tumors is due to their inability to elicit a T-helper cell response. James et al. (1993) *Clinical Immunology*, 4th edn., Lachmann et al. (eds), Blackwell Scientific Publications, Oxford. Thus, the expression of one or more cytokine genes, such as interleukin 2 (IL-2), tumor necrosis factor (TNF) and interferon, by tumor cells transduced with those genes, may avoid the need for T-helper cells. Fearon et al. (1990) *Cell* 60:397–403. A number of tumor vaccines have been described which involve ex vivo gene transduction of tumor cells with cytokine or major histocompatibility genes, and subsequent re-administration of the transduced cells. Tepper et al. (1994) *Hum. Gene Ther.* 5:153–164, Zatloukal et al. (1993) *Gene* 135:199–207, Clinical Protocols (1994) *Cancer Gene Ther.* 1:289–295, Gansbacher et al. (1990) *Cancer Res.* 50:7820–7825, Itaya et al. (1987) *Cancer Res.* 47:3136–3140. In particular, it has been shown that transduction with IL-2 genes affects nonimmunogenic or weakly immunogenic tumors cells by targeting those cells for destruction by the immune system. Schmidt et al. (1995) *Proc. Natl. Acad. Sci. USA* 92:4711–4714, Cavallo et al. (1992) *J. Immunol.* 149:3627–3635, Gansbacher et al. (1990) *J. Exp. Med.* 172:1217–1224.

Accordingly, the second gene of the AAV vectors can encode a cytokine, such as, but not limited to, human IL-2, interferons such as human $\alpha$-, $\beta$- or $\gamma$-interferon, human T-cell granulocyte-macrophage colony stimulating factor (GM-CSF), human tumor necrosis factor (TNF), and lymphotoxin (TNF-b). The human IL-2 gene has been cloned and sequenced and can be obtained as, for example, a 0.68 kB BamHI-HinDIII fragment from pBC12/HIV/IL-2 (available from the American Type Culture Collection ("ATCC") under Accession No. 67618). Further, the sequences of human $\beta$-interferon, human GM-CSF, human TNF and human lymphotoxin are known and are available. Particularly, the sequence of human $\beta$-interferon is known (Fiers et al. (1982) *Philos. Trans. R. Soc. Lond., B, Biol. Sci.* 299:29–38) and has been deposited with GenBank under Accession No. M25460. The sequence of human GM-CSF is known (Wong et al. (1985) *Science* 228:810–815) and has been deposited with GenBank under Accession No. M10663. The sequence of human TNF has been described (Wang et al. (1985) *Science* 228:149–154) and is deposited with GenBank under Accession No. M10988. The sequence of human lymphotoxin (TNF-b) has also been published (Iris et al. (1993) Nature Genet. 3:137–145) and is deposited with GenBank under Accession No. Z15026. The selected cytokine gene is used in the practice of the invention to enhance the immunogenicity of a transduced tumor cell. Further, the second gene can be a MHC class II gene which, when expressed, may assist in antigen presentation by the transduced tumor cells.

Alternatively, the second gene can be selected to provide a tumorstatic effect in a transduced tumor cell, such as wherein the second gene is a tumor suppressor gene. A number of tumor suppressor genes have been cloned and characterized, including RB1 (Toguchida et al. (1993) *Genomics* 17:535–543), p53 (Lamb et al. (1986) *Mol. Cell. Biol.* 6:1379–1385, Ewen et al. (1992) *Science* 255:85–87, Ewen et al. (1991) *Cell* 66:1155–1164, and Hu et al. (1990) *EMBO J.* 9:1147–1155), WT1 (Hastie, N. D. (1993) *Curr. Opin. Genet. Dev.* 3:408–413), NF1 (Trofatter et al. (1993) *Cell* 72:791–800, Cawthon et al. (1990) Cell 62:193–201), VHL (Latif et al. (1993) *Science* 260:1317–1320) and APC (Gorden et al. (1991) *Cell* 66:589–600).

Thus, the second gene included within the AAV vectors can be the human retinoblastoma associated (RB1) tumor suppressor gene. The sequence of RB1 is known (Friend et al (1987) *Proc. Natl. Acad. Sci. USA* 84:9059–9063) and is deposited with GenBank under Accession No. M33647. Alternatively, the second gene can be the human p53 gene. The p53 gene sequence is known (see e.g., Harris et al. (1986) *Mol. Cell. Biol.* 6:4650–4656) and is deposited with GenBank under Accession No. M14694. Further, a mutant p53 gene having wild-type activity can be used. For example, a murine 172-Leu mutant p53 has been described (Greenberg et al. (1994) *Cell Growth Differ.* 5:711–721). The subject mutant contains a single 172Arg→172Leu point mutation. Expression of the mutant p53 in transduced murine subjects results in radiation-induced apoptosis. A human analogue of the above-described murine mutant p53 gene can be used, wherein the human mutant has a point mutation at the 175Arg position, such as, but not limited to a 175Arg→175Leu point mutation, as well as any other amino acid substitution at this position which does not destroy the activity of the p53 gene product. The human mutant analogue can also include other minor variations from the native human sequence, particularly conservative amino acid replacements that do not adversely affect wild-type p53 biological function.

In an alternative embodiment of the invention, AAV vectors are provided which include a single gene, such as an interferon gene or a tumor suppressor gene. The AAV vectors can be used to provide either an immunogenic or a tumorstatic effect in a transduced solid tumor cell.

If desired, tissue-specific expression can be achieved by coupling the transduced gene or genes with heterologous control elements derived from genes that are specifically transcribed by a selected tissue type. Particularly, the probasin (PB) gene is known to be expressed specifically in the prostatic lobes, and is also detectable in the seminal vesicles. Matusik et al. (1986) *Biochem. & Cell Bio.* 64:601. A cDNA clone which contains the complete coding region for PB has been described. Spence et al. (1989) *Proc. Natl. Acad. Sci. USA* 86:7843. Further, the 5' probasin-flanking region has been shown to contain the necessary control sequences for prostatic targeting, and the region will thus direct prostate-specific expression of operably linked coding regions. Greenberg et al. (1993) *The Endocrine Society* June 9–11: Abstract 1206. In the practice of the invention, prostate-specific expression can be effected by coupling the 5'-flanking PB control sequences with the gene or genes of interest. Alternatively, tumor-specific expression can be achieved by coupling the transduced genes with control elements obtained from genes that are preferentially transcribed by tumors. Such control elements are termed "tumor-specific" herein. For example, the oncofetal protein carinoembryonic antigen (CEA) gene is often expressed at high levels in epithelial cancers and gastrointensional malignancies including colon and pancreatic tumors, but not in normal tissues. Warshaw et al. (1992) *N. Engl. J. Med.* 326:455–465. Thus, specific gene expression can be readily achieved using the transcriptional regulatory sequence or the promoter of CEA (CEA-P). A number of other suitable genes which are preferentially expressed in tumors have been described, and their promoters and/or other control elements can be included in the present AAV vector constructs to limit expression in non-tumor cells. Sikora, K. (1994) *Gene Therapy* 1:149–151, Huber et al. (1991) *Proc. Natl. Acad. Sci. USA* 88:8039–8043, Austin et al. (1993) *Mol. Pharmacol.* 43:380–387.

Examples of other tumor-specific control elements which are useful in the practice of the invention include, but are not limited to, the alpha-fetoprotein (AFP) control sequences (e.g., the promoter and enhancer) to target hepatomas and germ-cell tumors, neuron-specific enolase promoter to target small-cell lung cancer cells, dopa decarboxylase promoter to target neuroectodermal tumors, control sequences for glial fibro acidic protein (GFAP) to target gliomas, prostate-specific antigen (PSA) promoter to target prostate cancer, amylase promoter to target pancreatic cancer, insulin promoter to target pancreatic cancers, thyroglobulin promoter to target thyroid carcinoma, calcitonin promoter to target cancer of the medullary thyroid, promoters for tyrosinase or tyrosinase-related peptide to target melanomas, polymorphic epithelial mucin promoter to target breast cancer, villin promoter to target gastric cancer, gama-glutamyltranspeptidase promoter to target certain hepatic tumors, dopa decarboxylase to target certain lung tumors, c-erbB2 promoter to target breast and gastrointestinal cancer, c-erb3 promoter to target breast cancer, and c-erb4 promoter to target breast and gastric cancer.

In order to exemplify the present invention, an AAV vector including the HSV-tk gene and the human IL-2 gene was constructed. The exemplary AAV vector further includes an IRES (internal ribosome entry site) element interposed between the HSV-tk and human IL-2 genes. The sequence of picornaviral IRES elements are known (Hsieh et at. (1995) *Biochem. Biophys. Res. Commun.* 214:910–917), and an IRES element can be readily obtained from the 5' non-translated region of encephalomyocarditis virus (ECMV). A suitable IRES element can also be obtained from the 5' non-translated region of hepatitis C virus (HCV) (Wang et al. (1994) *J. Virol.* 68:7301–7307), or synthetically derived using known techniques. The IRES element allows for the efficient coexpression of both the HSV-tk and the IL-2 genes from the vector. Morgan et al. (1992) *Nucleic Acids Res.* 20:1293, Ghattas et al. (1991) *Mol. Cell Biol.* 11:5848. The IRES element thus avoids the need to provide two independent sets of control elements, with two promoters and two polyadenylation sequences. In particular, positioning the IRES element downstream of the translational stop codon of the first reading frame (e.g., the HSV-tk gene), directs ribosomal re-entry, thereby permitting initiation of translation at the start of the second reading frame (e.g., the IL-2 gene). This enables the use of a single promoter and polyadenylation signal to direct the expression of a bicistronic transcript that can be translated to provide both thymidine kinase and interleukin-2 within a single cell transduced with a single AAV vector. As described above, the contiguous nucleotide region containing the HSV-tk gene, the IRES and the IL-2 gene is flanked by AAV ITRs.

The selected nucleotide sequences are operably linked to control elements that direct the transcription or expression thereof in the subject in vivo. Each nucleotide sequence can be under the direction of a discrete set of control elements, or a single group of control elements can be used to direct the transcription or expression of both nucleotide sequences. A number of tissue-specific promoters have been described above which enable a more directed gene therapy for selected cancers. However, control elements used in the present vectors can also comprise control sequences normally associated with the selected genes. Alternatively, heterologous control sequences can be employed. Useful heterologous control sequences generally include those derived from sequences encoding mammalian or viral genes. Examples include, but are not limited to, the SV40 early promoter, mouse mammary tumor virus LTR promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, synthetic promoters, hybrid promoters, and the like. In addition, sequences derived from nonviral genes, such as the murine metallothionein gene, will also find use herein. Such promoter sequences are commercially available from, e.g., Stratagene (San Diego, Calif.).

The AAV vector which harbors the DNA of interest bounded by AAV ITRs, can be constructed by directly inserting the selected sequences into an AAV genome which has had the major AAV open reading frames ("ORFs") excised therefrom. Other portions of the AAV genome can also be deleted, so long as a sufficient portion of the ITRs remain to allow for replication and packaging functions. These constructs can be designed using techniques well known in the art. See, e.g., U.S. Pat. Nos. 5,173,414 and 5,139,941; International Publication Nos. WO 92/01070 (published Jan. 23, 1992) and WO 93/03769 (published Mar. 4, 1993); Lebkowski et al. (1988) Molec. Cell. Biol. 8:3988–3996; Vincent et al. (1990) Vaccines 90 (Cold Spring Harbor Laboratory Press); Carter, B. J. (1992) Current Opinion in Biotechnology 3:533–539; Muzyczka, N. (1992) Current Topics in Microbiol. and Immunol. 158:97–129; Kotin, R. M. (1994) Human Gene Therapy 5:793–801; Shelling and Smith (1994) Gene Therapy 1:165–169; and Zhou et al. (1994) J. Exp. Med. 179:1867–1875.

Alternatively, AAV ITRs can be excised from the viral genome or from an AAV vector containing the same and fused 5' and 3' of a selected nucleic acid construct that is present in another vector using standard ligation techniques, such as those described in Sambrook et al., supra. For example, ligations can be accomplished in 20 mM Tris-Cl pH 7.5, 10 mM $MgCl_2$, 10 mM DTT, 33 μg/mL BSA, 10 mM–50 mM NaCl, and either 40 μM ATP, 0.01–0.02 (Weiss) units T4 DNA ligase at 0° C. (for "sticky end" ligation) or 1 mM ATP, 0.3–0.6 (Weiss) units T4 DNA ligase at 14° C. (for "blunt end" ligation). Intermolecular "sticky end" ligations are usually performed at 30–100 μg/mL total DNA concentrations (5–100 nM total end concentration). AAV vectors which contain ITRs have been described in, e.g., U.S. Pat. No. 5,139,941. In particular, several AAV vectors are described therein which are available from the American Type Culture Collection ("ATCC") under Accession Numbers 53222, 53223, 53224, 53225 and 53226.

Additionally, chimeric genes can be produced synthetically to include AAV ITR sequences arranged 5' and 3' of the selected nucleic acid sequences. The complete chimeric sequence is assembled from overlapping oligonucleotides prepared by standard methods. See, e.g., Edge, Nature (1981) 292:756; Nambair et al. Science (1984) 223:1299; Jay et al. J. Biol. Chem. (1984) 259:6311.

In order to produce rAAV virions, an AAV vector that has been constructed as described above is introduced into a suitable host cell using known techniques, such as by transfection. A number of transfection techniques are generally known in the art. See, e.g., Graham et al. (1973) Virology, 52:456, Sambrook et al. (1989) Molecular Cloning, a laboratory manual, Cold Spring Harbor Laboratories, N. Y., Davis et al. (1986) Basic Methods in Molecular Biology, Elsevier, and Chu et al. (1981) Gene 13:197. Particularly suitable transfection methods include calcium phosphate co-precipitation (Graham et al. (1973) Virol. 52:456–467), direct micro-injection into cultured cells (Capecchi, M.R. (1980) Cell 22:479–488), electroporation (Shigekawa et al. (1988) BioTechniques 6:742–751), liposome mediated gene transfer (Mannino et al. (1988) BioTechniques 6:682–690), lipid-mediated transduction (Felgner et al. (1987) Proc. Natl. Acad. Sci. USA 84:7413–7417), and nucleic acid delivery using high-velocity microprojectiles (Klein et al. (1987) Nature 327:70–73).

For the purposes of the invention, suitable host cells for producing rAAV virions include microorganisms, yeast cells, insect cells, and mammalian cells, that can be, or have been, used as recipients of a heterologous DNA molecule. The term includes the progeny of the original cell which has been transfected. Thus, a "host cell" as used herein generally refers to a cell which has been transfected with an exogenous DNA sequence. Cells from the stable human cell line, 293 (readily available through, e.g., the ATCC under Accession No. ATCC CRL1573) are preferred in the practice of the present invention. Particularly, the human cell line 293 is a human embryonic kidney cell line that has been transformed with adenovirus type-5 DNA fragments (Graham et al. (1977) J. Gen. Virol. 36:59), and expresses the adenoviral E1a and E1b genes (Aiello et al. (1979) Virology 94:460). The 293 cell line is readily transfected, and provides a particularly convenient platform in which to produce rAAV virions.

2. AAV Helper Functions

Host cells containing the above-described AAV vectors must be rendered capable of providing AAV helper functions in order to replicate and encapsidate the nucleotide sequences flanked by the AAV ITRs to produce rAAV virions. AAV helper functions are generally AAV-derived coding sequences which can be expressed to provide AAV gene products that, in turn, function in trans for productive AAV replication. AAV helper functions are used herein to complement necessary AAV functions that are missing from the AAV vectors. Thus, AAV helper functions include one, or both of the major AAV ORFs, namely the rep and cap coding regions, or functional homologues thereof.

By "AAV rep coding region" is meant the art-recognized region of the AAV genome which encodes the replication proteins Rep 78, Rep 68, Rep 52 and Rep 40. These Rep expression products have been shown to possess many functions, including recognition, binding and nicking of the AAV origin of DNA replication, DNA helicase activity and modulation of transcription from AAV (or other heterologous) promoters. The Rep expression products are collectively required for replicating the AAV genome. For a description of the AAV rep coding region, see, e.g., Muzyczka, N. (1992) Current Topics in Microbiol. and Immunol. 158:97–129; and Kotin, R. M. (1994) Human Gene Therapy 5:793–801. Suitable homologues of the AAV rep coding region include the human herpesvirus 6 (HHV-6) rep gene which is also known to mediate AAV-2 DNA replication (Thomson et al. (1994) Virology 204:304–311).

By "AAV cap coding region" is meant the art-recognized region of the AAV genome which encodes the capsid proteins VP1, VP2, and VP3, or functional homologues thereof. These cap expression products supply the packaging functions which are collectively required for packaging the viral genome. For a description of the AAV cap coding region, see, e.g., Muzyczka, N. and Kotin, R. M. (supra).

AAV helper functions are introduced into the host cell by transfecting the host cell with an AAV helper construct either prior to, or concurrently with, the transfection of the AAV vector. AAV helper constructs are thus used to provide at least transient expression of AAV rep and/or cap genes to complement missing AAV functions that are necessary for productive AAV infection. AAV helper constructs lack AAV ITRs and can neither replicate nor package themselves.

These constructs can be in the form of a plasmid, phage, transposon, cosmid, virus, or virion. A number of AAV helper constructs have been described, such as the commonly used plasmids pAAV/Ad and pIM29+45 which encode both Rep and Cap expression products. See, e.g., Samulski et al. (1989) *J. Virol.* 63:3822–3828; and McCarty et al. (1991) *J. Virol.* 65:2936–2945. A number of other vectors have been described which encode Rep and/or Cap expression products. See, e.g., U.S. Pat. No. 5,139,941.

Both AAV vectors and AAV helper constructs can be constructed to contain one or more optional selectable markers. Suitable markers include genes which confer antibiotic resistance or sensitivity to, impart color to, or change the antigenic characteristics of those cells which have been transfected with a nucleic acid construct containing the selectable marker when the cells are grown in an appropriate selective medium. Several selectable marker genes that are useful in the practice of the invention include the gene encoding Aminoglycoside phosphotranferase (APH) that allows selection in mammalian cells by conferring resistance to G418 (available from Sigma, St. Louis, Mo.). Other suitable markers are known to those of skill in the art.

3. AAV Accessory Functions

The host cell (or packaging cell) must also be rendered capable of providing non AAV derived functions, or "accessory functions," in order to produce rAAV virions. Accessory functions are non AAV derived viral and/or cellular functions upon which AAV is dependent for its replication. Thus, accessory functions include at least those non AAV proteins and RNAs that are required in AAV replication, including those involved in activation of AAV gene transcription, stage specific AAV mRNA splicing, AAV DNA replication, synthesis of rep and cap expression products and AAV capsid assembly. Viral-based accessory functions can be derived from any of the known helper viruses.

Particularly, accessory functions can be introduced into and then expressed in host cells using methods known to those of skill in the art. Commonly, accessory functions are provided by infection of the host cells with an unrelated helper virus. A number of suitable helper viruses are known, including adenoviruses; herpesviruses such as herpes simplex virus types 1 and 2; and vaccinia viruses. Nonviral accessory functions will also find use herein, such as those provided by cell synchronization using any of various known agents. See, e.g., Buller et al. (1981) *J. Virol.* 40:241–247; McPherson et al. (1985) *Virology* 147:217–222; Schlehofer et al. (1986) *Virology* 152:110–117.

Alternatively, accessory functions can be provided using an accessory function vector. Accessory function vectors include nucleotide sequences that provide one or more accessory functions. An accessory function vector is capable of being introduced into a suitable host cell in order to support efficient AAV virion production in the host cell. Accessory function vectors can be in the form of a plasmid, phage, virus, transposon or cosmid. Accessory vectors can also be in the form of one or more linearized DNA or RNA fragments which, when associated with the appropriate control elements and enzymes, can be transcribed or expressed in a host cell to provide accessory functions.

Nucleic acid sequences providing the accessory functions can be obtained from natural sources, such as from the genome of adenovirus, or constructed using recombinant or synthetic methods known in the art. In this regard, adenovirus-derived accessory functions have been widely studied, and a number of adenovirus genes involved in accessory functions have been identified and partially characterized. See, e.g., Carter, B. J. (1990) "Adeno-Associated Virus Helper Functions," in *CRC Handbook of Parvoviruses*, vol. I (P. Tijssen, ed.), and Muzyczka, N. (1992) *Curr. Topics. Microbiol. and Immun.* 158:97–129. Specifically, early adenoviral gene regions E1a, E2a, E4, VAI RNA and, possibly, E1b are thought to participate in the accessory process. Janik et al. (1981) *Proc. Natl. Acad. Sci. USA* 78:1925–1929. Herpesvirus-derived accessory functions have been described. See, e.g., Young et al. (1979) *Prog. Med. Virol.* 25:113. Vaccinia virus-derived accessory functions have also been described. See, e.g., Carter, B. J. (1990), supra., Schlehofer et al. (1986) *Virology* 152:110–117.

As a consequence of the infection of the host cell with a helper virus, or transfection of the host cell with an accessory function vector, accessory functions are expressed which transactivate the AAV helper construct to produce AAV Rep and/or Cap proteins. The Rep expression products direct excision of the recombinant DNA (including the DNA of interest) from the AAV vector. The Rep proteins also serve to duplicate the AAV genome. The expressed Cap proteins assemble into capsids, and the recombinant AAV genome is packaged into the capsids. Thus, productive AAV replication ensues, and the DNA is packaged into rAAV virions.

Following recombinant AAV replication, rAAV virions can be purified from the host cell using a variety of conventional purification methods, such as CsCl gradients. Further, if helper virus infection is employed to express the accessory functions, residual helper virus can be inactivated, using known methods. For example, adenovirus can be inactivated by heating to temperatures of approximately 60° C. for, e.g., 20 minutes or more. This treatment selectively inactivates the helper adenovirus which is heat labile, while preserving the rAAV which is heat stable.

The resulting rAAV virions are then ready for use for DNA delivery to a variety of solid tumor cell types.

4. In vivo Delivery of rAAV Virions

Generally, rAAV virions are introduced into a tumor cell using in vivo transduction techniques. Particularly, for in vivo delivery, the rAAV virions will be formulated into pharmaceutical compositions and generally administered by injection directly into a tumor mass, injected intravenously into blood veins feeding the tumor mass, or administered into a tumor bed after debulking. Preferably, the rAAV virions are administered by applying a pharmaceutical composition containing rAAV virions directly to a tumor bed after surgical resection procedures have been used to debulk tumor mass. If desired, an Omaya reservoir can be placed within the surgical site to enable repeat administration of rAAV virions.

Alternatively, precise delivery of rAAV virions into tumor sites, e.g., into gliomas or other intracranial tumors, can be conducted using stereotactic microinjection techniques. For example, the subject being treated can be placed within a stereotactic frame base (MRI-compatible) and then imaged using high resolution MRI to determine the three-dimensional positioning of the particular tumor being treated. The MRI images are then transferred to a computer having the appropriate stereotactic software, and a number of images are used to determine a target site and trajectory for rAAV virion microinjection. The software translates the trajectory into three-dimensional coordinates that are appropriate for the stereotactic frame. In the case of intracranial delivery, the skull will be exposed, burr holes will be drilled above the entry site, and the stereotactic apparatus positioned with the needle implanted at a predetermined depth. If desired, de-bulking operations can be carried out prior to positioning of the stereotactic apparatus. A pharmaceutical composition containing an rAAV virion can then be microinjected at the selected target sites. Spread of the rAAV virion from the site of injection will be a function of passive diffusion which may be controlled by adjusting the ratio of the recombinant virion in the pharmaceutical composition.

Pharmaceutical compositions will comprise sufficient genetic material to produce a therapeutically effective amount of the drug sensitizing protein. Furthermore, in those applications where a cytokine gene is included in the rAAV virion, the compositions will include an amount of the cytokine or biological response modifier gene that is sufficient to confer the desired benefit. The pharmaceutical compositions will also contain a pharmaceutically acceptable excipient. Such excipients include any pharmaceutical agent that does not itself induce an immune response harmful to the individual receiving the composition, and which may be administered without undue toxicity. Pharmaceutically acceptable excipients include, but are not limited to, liquids such as water, saline, glycerol and ethanol. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles. A thorough discussion of pharmaceutically acceptable excipients is available in REMINGTON'S PHARMACEUTICAL SCIENCES (Mack Pub. Co., N.J. 1991).

Appropriate doses will depend, among other factors, on the mammal being treated (e.g., human or nonhuman primate or other mammal), age and general condition of the subject to be treated, the severity of the cancer being treated, the selected therapeutic genes employed and their mode of administration. An appropriate effective amount can be readily determined by one of skill in the art.

Thus, a "therapeutically effective amount" will fall in a relatively broad range that can be determined through clinical trials. For example, in the case of in vivo transductions, i.e., injection directly into the cancerous tissue, a therapeutically effective dose will be on the order of from about $10^3$ to $10^{15}$ of the rAAV virions. Other effective dosages can be readily established by one of ordinary skill in the art through routine trials establishing dose response curves.

Dosage treatment may be a single dose schedule or a multiple dose schedule. Moreover, the subject may be administered as many doses as appropriate. One of skill in the art can readily determine an appropriate number of doses.

After solid tumor cells have been transduced, the appropriate cytotoxic agent is administered to the subject. Appropriate cytotoxic agents include, but are not limited to, the relatively nontoxic prodrugs ganciclovir, aciclovir, 6-methoxypurine arabino-nucleoside, cyclophosphamide, cytosine arabinoside, and 5-fluorocytosine. In particular, the HSV-tk expression product converts specific protoxic nucleoside analogues, such as acyclovir and ganciclovir, to monophosphate intermediates that are then phosphorylated by cellular kinases to provide potent DNA synthesis inhibitors. Cells capable of expressing HSV-tk are thus rendered extremely sensitive to the toxic effect of ganciclovir. The varicella-zoster virus-tk expression product confers sensitivity to the prodrug 6-methoxypurine arabinonucleoside. Huber et al. (1991) *Proc. Natl. Acad. Sci. USA* 88:8039–8043.

The prodrug cyclophosphamide, an alkylating agent with activity against a variety of tumors, requires metabolism by hepatic cytochrome P450 to produce the pharmacologically active metabolites 4-hydroxy-cyclophosphamide (4-HOCPA) and phosphoramide mustard. Colvin et al. (1981) *Cancer Treat Rep* 65:89–95, and Sladek et al. (1987) *Metabolism and Action of Anti-Cancer Drugs*, Powis et al. eds., Taylor and Francis, New York, N.Y., pp 48–90. Cells capable of expressing cytochrome P450 are thus rendered sensitive to the toxic effect of cyclophosphamide.

Cytosine arabinoside (ara-C) is an effective anti-cancer agent that incorporates into replicating DNA and terminates DNA chain elongation. Graham et al. (1970) *Cancer Res.* 30:2636–2644, Kufe et al. (1980) *J. Biol. Chem.* 225:8997–9000, Kufe et al. (1984) *Blood* 64:54–58, and Early et al. (1982) *Cancer Res.* 42:1587–1594. Pharmacologic properties of ara-C that are particularly suited for treatment of central nervous system tumors include penetration across the blood-brain barrier, and a relative lack of toxicity against postmitotic cells. However, resistance mechanisms, such as the rapid deamination of ara-C by cytidine deaminase as compared with phosphorylation to the active ara-CMP molecule by deoxycytidine kinase (dCK), must be overcome to enhance the effect of the drug. Cells that are transduced with the deoxycytidine kinase gene can thus be rendered much more sensitive to the cytotoxic effects of ara-C by shifting the balance toward the production of ara-CMP.

The bacterial cytosine deaminase (cd) gene functions to deaminate cytosine to uracil (Danielson et al. (1992) *Mol. Microbiol.* 6:1335–1344). Through a similar mechanism, the expression product of cd can deaminate the nucleoside prodrug, 5-fluorocytosine (5-FC) to the cytotoxic agent 5-fluorouracil (5-FU). Since mammalian cells do not normally carry the cd gene, 5-FC is generally nontoxic, even in high concentrations. Cells capable of expressing bacterial cytosine deaminase are thus rendered sensitive to the toxic effect of 5-fluorocytosine.

The cytotoxic agent will be administered systemically, usually by intravenous injection. For example, ganciclovir sodium (GCV) can be obtained from Roche, Basel, Switzerland (under the trade name DENOSINE®) or from Syntex Corporation, Palo Alto, Calif. (under the trade name of Cytovene®). GCV can be administered by intravenous infusion over 1 hour at a dose of from about 5 mg/kg to 10 mg/kg of body weight twice daily for 14–21 days post-transduction. In regard to the treatment of gliomas, GCV is capable of crossing the blood-brain barrier. Cerebral spinal fluid (CSF)/plasma ratios have been estimated in 3 patients (Oldfield, E.H. (1993) *Hum. Gene Ther.* 4:39–69) at various time intervals, and found to range from about 0.24 to 0.7 (e.g., 0.31–0.68 µg/mL in the CSF and 0.44–2.20 µg/mL in the plasma). Therapeutically effective amounts of other cytotoxic agents, and dosing regimens can be determined by those of skill in the art through routine trials.

C. Experimental

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

1. Vector Constructs

A. Construction of WadhlacZ and p1909adhlacZ

Plasmid p1909adhlacZ was used as a helper/vector construct in the following examples and was constructed from plasmid pWadhlacZ. Plasmid pWadhlacZ was constructed by partially digesting plasmid pUC119 (GenBank Reference Name: U07649, GenBank Accession Number: U07649) with AflIII and EspHI, blunt-end modifying with the klenow enzyme, and then ligating to form a circular 1732 bp plasmid containing the bacterial origin and the amp gene only (the polylinker and F1 origin were removed). The blunted and ligated AflIII and EspHI junction forms a unique NspI site. The 1732 bp plasmid was cut with NspI, blunt-end modified with T4 polymerase, and a 20 bp HinDIII-HinCII fragment (blunt-end modified with the klenow enzyme) obtained from the pUC119 polylinker was ligated into the blunted NspI site of the plasmid. The HinDIII site from the blunted polylinker was regenerated, and then positioned adjacent to the bacterial origin of replication. The resulting plasmid was then cut at the unique PstI/Sse8387I site, and an Sse8387I-PvuII-Sse8387I oligonucleotide (5'-GGCAGCTGCCTGCA-3') (SEQ ID NO:1) was ligated in. The remaining unique BspHI site was cut, blunt-end modified with klenow enzyme, and an oligonucleotide containing an AscI linker (5'-GAAGGCGCGCCTTC-3') (SEQ ID NO:2) was ligated therein, eliminating the BspHI site. The resulting plasmid was called pwee.

In order to create pWadhlacZ, a CMVlacZ expression cassette (comprising a nucleotide sequence flanked 5' and 3' by AAV ITRs, containing the following elements: a CMV promoter, the hGH 1st intron, an alcohol dehydrogenase LacZ ("adhlacZ") fusion obtained from Stratagene, San Diego, Calif. as the pCMV-β construct, and an SV40 early polyadenylation site) was inserted into the unique PvuII site of pwee using multiple steps such that the CMV promoter was arranged proximal to the bacterial amp gene of pwee.

More particularly, a CMVlacZ expression cassette was derived from the plasmid psub201CMV, which was constructed as follows. An oligonucleotide encoding the restriction enzyme sites: NotI-MuI -SnaBI-AgeI-BstBI-BssHII-NcoI-HpaI-BspEI-PmlI-RsrII-NotI and having the following nucleotide sequence: 5'-GCGGCCGCACGCGT-ACGTACCGGTTCGAAGCGCGCACGGCCGACCATGG-TTAACTCCGGACACGTGCGGACCGCGGCCGC-3' (SEQ ID NO:3) was synthesized and cloned into the blunt-end modified KasI-EarI site (partial) of pUC119 to provide a 2757 bp vector fragment. A 653 bp SpeI-SacII fragment containing a nucleotide sequence encoding a CMV immediate early promoter was cloned into the SnaBI site of the 2757 bp vector fragment. Further, a 269 bp PCR-produced BstBI-BstBI fragment containing a nucleotide sequence encoding the hGH 1st intron which was derived using the following primers: 5'-AAAATTCGAACCT-GGGGAGAAACCAGAG-3' (SEQ ID NO:4) and 3'-aaaattcgaacaggtaagcgccctTTG-5' (SEQ ID NO:5), was cloned into the BstBI site of the 2757 bp vector fragment, and a 135 bp HpaI-BamHI (blunt-end modified) fragment containing the SV40 early polyadenylation site from the pCMV-β plasmid (CLONETECH) was cloned into the HpaI site of the subject vector fragment. The resulting construct was then cut with NotI to provide a first CMV expression cassette.

Plasmid pW1909adhlacZ was constructed as follows. A 4723 bp SpeI-EcoRV fragment containing the AAV rep and cap encoding region was obtained from the plasmid pGN1909 (ATCC Accession Number 69871). The pGN1909 plasmid is a high efficiency AAV helper plasmid having AAV rep and cap genes with an AAV p5 promoter region that is arranged in the construct to be downstream from its normal position (in the wild type AAV genome) relative to the rep coding region. The 4723 bp fragment was blunt-end modified, and AscI linkers (5'-GAAGGCGCGCCTTC-3') (SEQ ID NO:2) were ligated to the blunted ends. The resultant fragment was then ligated into the unique AscI site of pWadhlacZ and oriented such that the AAV coding sequences were arranged proximal to the bacterial origin of replication in the construct.

Plasmid pW1909adhlacZ includes the bacterial beta-galactosidase (β-gal) gene under the transcriptional control of the cytomegalovirus immediate early promoter (CMVIE).

B. Construction of p1.1ctk-IRES-hIL-2 and pW1909tk-IRES-hIL-2

The pW1909tk-IRES-hIL2 vector contains the herpes-simplex virus thymidine kinase (HSV-Tk) coding region, an IRES (internal ribosome entry site) sequence arranged 3' of the HSV-Tk coding region, and the human interleukin-2 gene arranged 3' of the IRES sequence. The molecule containing these sequences is flanked by AAV ITRs.

Particularly, pUC119 was partially digested with KasI and EarI, and a 2713 bp vector fragment containing the ampicillin resistance gene, the coli 1 origin of replication and the M13 origin of replication, was isolated, blunt end modified, and ligated to a synthetic DNA polylinker encoding the restriction enzyme sites NotI-MluI-SnaBI-AgeI-SfuI-BssHII-EagI-NcoI-PmeI-BspEI-PmlI-RsrII-NotI, and having the following nucleotide sequence: 5'-GCGGCCG-CACGCGTTGTTAACAACCGGTTCGAAGCGCG CAGCGGCCGACCATGGGTTTAAACTCCGGACCAC-GTGCGGACCGAGCGGCCGC-3' (SEQ ID NO:6). The ligation was conducted such that the MluI end of the polylinker was ligated to the KasI side of the plasmid. A 653 bp SpeI-SacII fragment encoding the CMV immediate-early promoter, a 269 bp PCR-produced SfuI-SfuI produced fragment encoding the hGH 1st intron (derived using the following primers: 5'-AAAATTCGAACAGGTAA-GCGCCCTTTG-3' (SEQ ID NO:7) and 3'-AAAATTCGAACCTGGGGAGAAACCAGAG-5' (SEQ ID NO:8)), a 183 bp BssHII-BssHII polylinker fragment from pbluescript II SK-, and a 135 bp HpaI-BamHI (blunted) fragment containing the SV40 early polyadenylation site from pCMV-β (Stratagene), were cloned into the SnaBI, SfuI, BssHII, and PmeI sites, respectively, of the aforementioned plasmid. The orientation of the polylinker relative to the intron and polyadenylation site was intron-polylinker (5'SacI-3'KpnI)-polyadenylation site. The polylinker was further modified by removing the 88 bp SacI-XhoI polylinker fragment and replacing it with the following synthetic SacI to XhoI fragment encoding the restriction enzyme sites SacI-ClaI-EcoRI-SmaI-BamHI-XbaI-SalI-PstI-BstXI-EcoRV-BstXI-omeganuclease-HinDIII-XhoI, having the following nucleotide sequence: 5'-GAGCTCAATCGATTGAATTCCCCGGGGATCCTCT-AGAGTCGACCTGCAGCCACTGTGTTGGATA-TCCAACACACTGGTAGGGATAACAGGGTAATCT-CGAG-3' (SEQ ID NO:9). This plasmid was named p1.1c.

Restriction fragments encoding the HSV thymidine kinase (tk) gene (a 1827 bp BglII-FseI fragment corresponding to bases 47,855–46,028 of the HSV-1 genome), the human encephalomyocarditis virus internal ribosome entry site (ECMV-IRES) element (a 582 bp EcoRI-MseI fragment from pBS-ECAT (Jang et al. (1989) *J. Virol.* 63:1651–1660)), and the human interleukin-2 (hIL-2) cDNA (a 0.68 kb BamHI-HinDIII fragment from pBC12/HIV/IL-2 (available from the ATCC under Accession No.: 67618), were blunt end modified and cloned into the SmaI, HinCII, and EcoRV sites of p1.1c, respectively. M13 phagemid-based, in vitro mutagenesis was then used to remove the 3' untranslated regions of the tk gene, and to remove the sequences between the initiator ATG of the IRES and the second codon of the hIL-2 signal sequence, using the following mutagenic oligonucleotides: 5'-GGGGAGGCTAACTGAGCGGGGATCCTCTAGAG-3' (SEQ ID NO:10) and 5'-AAACACGATGATAATAT-GGCCCTGTGGATC-3' (SEQ ID NO:11). The resulting plasmid was called p1.1ctk-IRES-hIL-2. An AAV vector production plasmid, pW1909tk-IRES-hIL-2 was created by moving the 3513 bp NotI-NotI fragment encoding the expression cassette from p1.1ctk-IRES-hIL-2 into the vector portion of pW1909adhlacZ cut with NotI (to remove the lacZ expression cassette). To give the construct an appropriate packaging size, a 737 bp fragment obtained from the commercially available plasmid pMC1871 (Pharmacia) was added 3' of the IL-2 gene. Particularly, pMC1871 was digested with EcoRI and BglII, blunted with T4 polymerase, and the resulting blunted fragment was cloned into the klenow-blunted RsrII site on pW1909tk-IRES-hIL-2.

C. Construction of pW1909IFN-β

The human IFN-β gene was obtained from plasmid pSV2IFN-β, available from Toray Industries, Toyko, Japan. pSV2IFN-β was digested with XbaI and ApaI to obtain a fragment containing the IFN-β gene and the SV40 polyadenylation signal. The fragment was then cloned into p1.1c at the XbaI and ApaI sites to create the plasmid pl.lcIFN-β.

In order to increase the size of the gene construct for efficient packaging, a segment of the β-galactosidase gene was added as a non-coding spacer fragment. Particularly, pCMVβ (Clonetech) was digested with HpaI to obtain a 624 bp blunted fragment. The blunt fragment was cloned into the blunt BbrP1 site in p1.1cIFN-β to create the plasmid p1.1cIFN-β-spacer. The resulting plasmid was then digested with NotI, and the entire gene cassette, including the CMV promoter from p1.1c, IFN-β, the SV40 polyadenylation signal from pSV2IFN-β, and the LacZ spacer from pCMV-β, was cloned into the NotI site of pW1909 to obtain pW1909IFN-β. Cloning into the NotI site of pW1909 places the gene cassette between AAV ITRs.

Viruses and Cell Culture

Adenovirus type-2 (Ad-2), available from the ATCC under Catalogue No. VR846, was used as helper virus to encapsidate the recombinant virions.

The human 293 cell line (Graham et al. (1977) *J. Gen. Virol.* 36:59–72, available from the ATCC under Accession No.: CRL1573), which has adenovirus E1a and E1b genes stably integrated in its genome, was cultured in complete Dulbecco's modified Eagle's media (DMEM; Bio-Whittaker, Walkersville, Md.) containing 4.5 g/L glucose, 10% heat-inactivated fetal bovine serum (FBS; Hyclone, Logan, Utah), 2 mM glutamine, and 50 units/mL penicillin and 50 μg/mL streptomycin.

The human glioma U-251SP cell line, which is a subclone of the human glioma cell line U-251MG (Ponten et al. (1967) *Int. J. Cancer* 2:434), was maintained in culture in Dulbecco's modified Eagle's medium (DMEM, GIBCO, Paisley, UK) supplemented with 10% fetal calf serum, streptomycin (100 μg/mL), penicillin (100 U/mL), 2 mM L-glutamate and nonessential amino acids.

Production of Recombinant AAV Virions

Recombinant AAV virions were produced in human 293 cells as follows. Subconfluent 293 cells were transfected by calcium phosphate precipitation with one of the following plasmid constructs pW1909adhLacZ, pW1909tk-IRES-hIL2, or pW1909IFN-β. The cells were then infected with Ad2 at a multiplicity of infection (MOI) of 2, and incubated at 37° C. in 5% $CO_2$ for 70 hours prior to harvest. After the incubation, the cells were lysed in Tris buffer (100 mM Tris, 150 mM NaCl, pH 8.0), freeze-thawed three times, and the crude-cell lysate was layered onto a cesium chloride cushion for isopycnic gradient centrifugation. Recombinant AAV virions (e.g., rAAVlacZ, rAAVtk-IRES-hIL2 or rAAVIFN-β) were extracted from the resulting gradient by isolating the bands with average density of approximately 1.38 g/mL, resuspended in HEPES buffered saline (HBS) containing 50 mM Hepes, 150 mM NaCl, pH 7.4, and heat-inactivating the preparation at 56° C. for 1 hour.

Assay of rAAV by Dot-blot Hybridization

Recombinant AAV virions were DNase I digested, proteinase K treated, phenol-chloroform extracted, and DNA precipitated with sodium acetate-glycogen (final concentrations of 0.3M sodium acetate and 160 μg/mL, respectively). DNA samples were denatured by adding 200 μL of 2× alkaline solution (0.8 M NaOH), and 20 mM EDTA to the DNA sample for 10 minutes. Denatured DNA samples were then added to appropriate wells in a dot-blot apparatus and blotted to wet ZETA PROBE® membranes (available from BioRad, Richmond, Calif.), by applying suction until wells were empty. 400 μL of 1× alkaline solution was then added, and after 5 minutes, the wells were emptied by suction. The membranes were rinsed in 2× SSC (Sambrook et al., supra) for 1 min, drained, air dried on filter paper, then baked in vacuum at 80° C. for 30 min. Membranes were then prehybridized for 30 min at 65° C. with 10 mL hybridization buffer (7% SDS, 0.25 M Sodium Phosphate, pH 7.2, 1 mM EDTA). Buffer was replaced with 10 mL fresh solution, freshly boiled probe added, and hybridized overnight at 65° C. For rAAVtk-IRES-hIL2 and rAAVlacZ, the probes used in the hybridizations were a $^{32}$P-labeled 737 bp EcoRI-BglI fragment obtained from the LacZ gene. For rAAVIFN-β, the probe used in the hybridization was a Not-NotI fragment obtained from the pW1909IFN-β plasmid. However, to probe all three constructs, the 3103 bp SalT-SalI fragment from pMC1871 can be used to hybridize the LacZ gene in rAAVLacZ, and the LacZ-derived spacer fragments present in rAAVtk-IRES-hIL2 and rAAVIFN-β. The membranes were washed twice with 25 mL of wash-1 buffer (5% SDS, 40 mM sodium phosphate, pH 7.2, 1 mM EDTA) for 20 min at 65° C. and twice with wash-2 buffer (1% SDS, 40 mM sodium phosphate, pH 7.2, 1 mM EDTA). The membranes were wrapped in plastic film, exposed to radiographic film, and appropriate dots were excised to determine radioactivity by scintillation counting, and quantitated by comparison with standards.

The titers of the recombinant virion stocks were $3 \times 10^{13}$/mL (rAAVtk-IRES-hIL2), $1.6 \times 10^{13}$/mL (rAAVlacZ), and $1.9 \times 10^{13}$/mL (rAAVIFN-β) as determined by quantitative DNA hybridization. These titers do not represent actual infectious titers, which, in the case of AAVLacZ in 293 cells, was approximately $1 \times 10^9$/mL in a transient expression assay.

Assay for Contaminating Helper Adenovirus

Contaminating infectious adenovirus was assayed as follows. Samples from the purified rAAV virion stocks were added to 50% confluent 293 cells (cultured in 12 well dishes at $1 \times 10^5$ cells/well), and the cultures were passaged for 30 days (e.g., the cultures were split 1 to 5, every 3 days) or until the culture exhibited 100% cytopathic effect (CPE) due to adenovirus infection. Cultures were examined daily for CPE, and the day upon which each experimental culture showed 100% CPE was noted. Reference 293 cell cultures infected with a range of known amounts of adenovirus type-2 (from 0 to $1 \times 10^7$ plaque forming units (pfu)/culture) were also prepared and treated in the same manner. A standard curve was then prepared from the data obtained from the reference cultures, where the adenovirus pfu number was plotted against the day of 100% CPE. The titer of infectious adenovirus type-2 in each experimental culture was then readily obtained as determined from the standard curve. The limit of detection of the assay was 100 pfu/mL. The presence of wild-type AAV contamination, analyzed by dot-blot hybridization, was at least 7 logs lower than recombinant virion concentration.

Histochemical Staining of LacZ-Transduced Cells

Glass slides having cultured cells or tumor tissue sections were fixed for 10 minutes in X-Gal fixative solution (phosphate-buffered saline (PBS), pH 7.4, 2% formaldehyde, and 0.2% glutaraldehyde) at 4° C., and stained for β-gal activity as described (Sanes et al. (1986) "Use of Recombinant Retrovirus to Study Post-Implantation Cell Lineage in Mouse Embryos," *EMBO J* 5:3133–3142). More particularly, the fixed samples were immersed in X-Gal staining solution (PBS, 5 mM $K_4Fe[CN]_6$, 5 mM $K_3Fe_3[CN]_6$, 2 mM $MgCl_2$) and 1 mg/mL X-Gal stain (5-bromo-4-chloro-3-indolyl β-D-galactoside, available from Gold Biotechnology, St. Louis, Mo.) for 24 hours at 37° C. and counterstained with hematoxylin and eosin (H&E).

EXAMPLE 1

Efficacy of In Vitro Transduction of Glioma Cells with rAAV Virions

In order to assess the transduction efficiency of rAAV virions produced in accordance with the invention, the following study was carried out. In vitro transductions were performed by adding purified rAAV virions to human U-251SP glioma cells cultured in complete media, and incubating for the designated period of time. More particularly, aliquots of about $1-3\times10^4$ U-251SP cells were plated into each well of 24 well plates (Falcon 3047, Becton Dickinson, Lincoln Park, N.J.) with 500 μL of complete medium. Sterile coverslips were placed on the bottoms of the wells for those cells to be transduced by rAAVLacZ virions. Twelve hours later, recombinant AAVLacZ or AAVtk-IRES-hIL2 virions were added to each well and incubation continued to 12 hours. The medium was then changed and various concentrations of ganciclovir (DENOSINE® Roche, Basel, Switzerland) were added to the cells transduced with rAAVtk-IRES-hIL2. Approximately 72 hours later, living cells were counted in both experimental groups using the trypan blue dye exclusion method.

Cells transduced with the rAAVLacZ virion were also stained at different time periods with X-Gal to reveal β-galactosidase expression using the methods described above.

Referring now to FIG. 1, particularly parts (A), (B), (C), and (F), the transduction frequency at 48 hours after transduction achieved with various concentrations of rAAVLacZ virions was assessed. The cells in part (A) were transduced at a MOI of $3\times10^5$, the cells in part (B) at a MOI of $3\times10^4$, the cells in part (C) at a MOI of $3\times10^3$, and the cells in part (F) at a MOI of 0. As can be seen, nearly 100% transduction efficiency was achieved in those cells infected at a MOI of $3\times10^5$, approximately 60% at a MOI of $3\times10^4$, and 6 to 8% at a MOI of $3\times10^3$.

Referring now to FIG. 1, parts (D) and (E), the ability of transduced cells to provide long term expression of the transduced LacZ gene was determined. Particularly, the cells in parts (D) and (E) were each transduced with rAAVLacZ virions at a MOI of $3\times10^5$, and cultured in the exponentially growing state for either 7 days or 42 days, respectively. X-Gal staining in the 42 day culture was performed once per week after day 7 to monitor LacZ expression (data not shown). As can be seen, about 50% of cells continued to express LacZ at day 7 (see part (D)), and approximately 8 to 10% continued to express LacZ at day 42 (see part (E)), suggesting that about 10% of the transduced cells had stably integrated the rAAV virion.

Furthermore, the effect of the recombinant virions alone on the cells was assessed by transducing $1\times10^4$ human U-251SP glioma cells/well (cultured in 200 μL of complete medium) with rAAVLacZ virions at various MOIs. The cells were incubated without medium change, and the number of viable cells were counted using the trypan blue dye exclusion method on days 2 and 4. An 18% growth inhibition was seen 4 days after inoculation in cells transduced at a MOI of $2\times10^6$ which is much higher than the lowest MOI found to provide nearly 100% transduction efficiency ($3\times10^5$) as described above.

EXAMPLE 2

In Vitro Sensitivity of rAAV-Transduced Cells to Ganciclovir

In order to determine if cells transduced with the HSV-tk gene had enhanced susceptibility to the cytocidal effects of GCV, the following study was carried out. Recombinant AAV virion-transduced cells were exposed to varying amounts of GCV to assess their sensitivity to the drug. Particularly, $1\times10^4$ human U-251SP glioma cells/well (cultured in 200 μL of complete medium) were incubated with various concentrations of rAAVtk-IRES-hIL2 (at MOIs of 0, $3\times10^2$, $3\times10^3$, $3\times10^4$, $3\times10^5$, and $3\times10^6$) for 12 hours. The transduced cells were then incubated for an additional 72 hours in fresh medium containing serial dilutions of GCV at a final concentration of from 0.1–100 μg/mL. The numbers of living cells were then determined using the trypan blue dye exclusion method, and compared with those of nontransduced cells cultured without GCV treatment.

Figure 2:
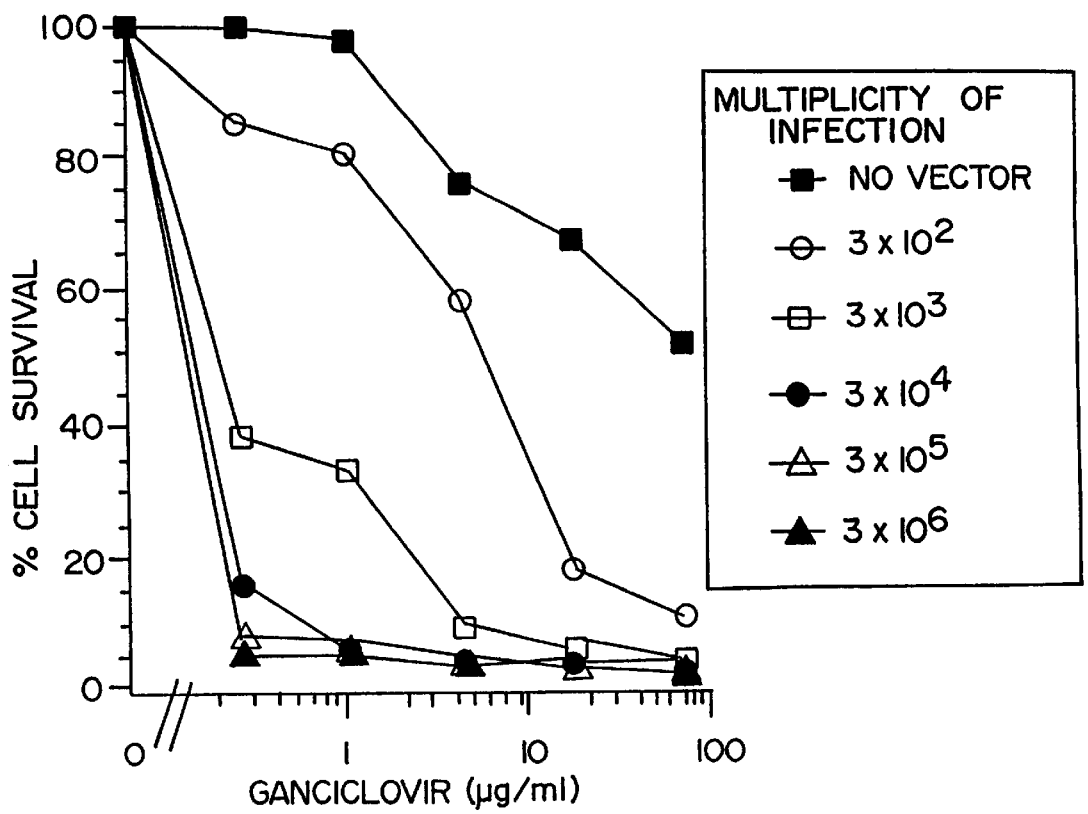
FIG. 2 shows the effects of ganciclovir (GCV) on cells that were transduced with the herpes simplex virus thymidine kinase (HSV-tk) gene as described in Example 2. More particularly, transduced cells were exposed to varying amounts of GCV to assess their sensitivity to the pro-drug. In the study $1 \times 10^4$ human U-251SP glioma cells were incubated for 12 hours with rAAVtk-IRES-hIL2 at MOIs of 0, $3 \times 10^2$, $3 \times 10^3$, $3 \times 10^4$, $3 \times 10^5$, and $3 \times 10^6$. The transduced cells were then incubated for an additional 72 hours in fresh medium containing serial dilutions of GCV at a final concentration of from 0.1–100 μg/mL. Numbers of living cells were then counted and compared with those of cultures of nontransduced cells that also did not receive GCV.

Referring now to FIG. 2, the % cell survival of each transduction group over the range of GCV dilutions is depicted. As can be seen, a TCID50 was obtained using less than about 0.28 μg/mL GCV in those cells exposed to the recombinant virions at a MOI of $3\times10^3$ or greater. With those cells exposed to 4.5 μg/mL of GCV, more than 80% inhibition could be achieved at a MOI of $3\times10^3$. Exposure to high doses of GCV in non-transduced cells had a mild inhibitory effect on the cell growth. Since the transduction efficiency of rAAVLacZ has been estimated to be around 10% at a MOI of $3\times10^3$ (see FIG. 1C), these data strongly suggest that cell death of the non-transduced glioma cells is mediated by the bystander cytocidal effect as previously reported.

EXAMPLE 3

Assay of In Vitro Bystander Tumoricidal Effect

In order to assess the in vitro bystander tumoricidal effect of HSV-tk transduced cells on neighboring non-transduced cells, the following study was carried out. U-251SP cells were incubated for 12 hours in DMEM medium containing rAAVtk-IRES-hIL2 virions at a MOI of 1. $9\times10^6$. Since this MOI was greater than the MOI determined necessary for 100% transduction by the rAAVlacZ virions (e.g., $3\times10^5$ as determined above in Example 1), the incubated cells were considered to be 100% transduced. The rAAVtk-IRES-hIL2 transduced cells were cocultured with non-transduced U-251SP cells at ratios of 1:0, 1:1, 1:10, 1:100 and 0:1 (transduced:nontransduced cells) to provide $1 \times 10^4$ total cells per well in a 24 well tissue culture plate. 24 hours after the coculture was initiated, 4.5 µg/mL of ganciclovir (DENOSINE® Roche, Basel, Switzerland) was added to each well in fresh media. After 3 days, the numbers of living cells were determined using the trypan blue dye exclusion method.

Figure 3:
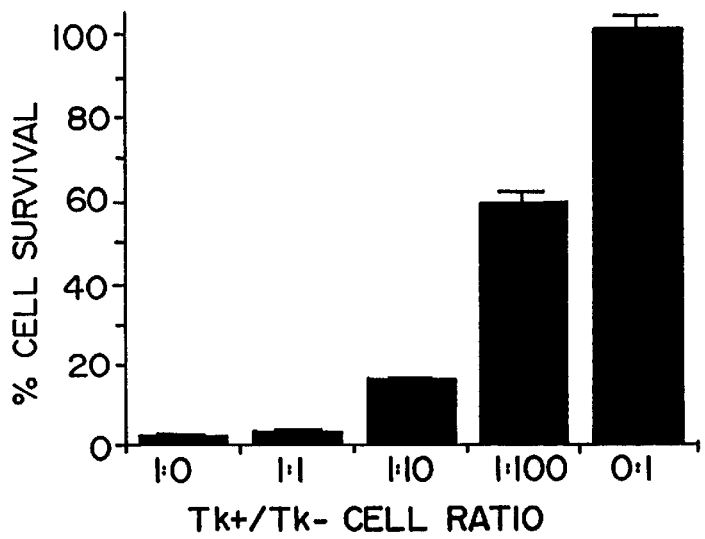
FIG. 3 depicts the in vitro cytocidal bystander effect observed in non-transduced cells that were cultured with HSV-tk transduced cells as described in Example 3. Cell co-cultures containing a total of $1 \times 10^4$ cells were formed by combining cells that were transduced with rAAVtk-IRES-hIL2 virions at the following ratios: 1:0, 1:1, 1:10, 1:100 and 0:1 (transduced:nontransduced cells). After a 24 hour incubation, the co-cultures were exposed to 4.5 μ/mL of ganciclovir and allowed to incubate for an additional 3 days. Numbers of living cells were counted using the trypan blue dye exclusion method. The Figure indicates % cell survival compared to the cultures containing only non-transduced cells (0:1). The data is presented a mean ± a standard error deviation based on duplicate experiments.

Referring now to FIG. 3, cocultures containing 50% transduced cells (1:1) were as sensitive to GCV killing as were cultures containing 100% transduced cells (1:0). Proliferation in cultures containing 10% or 1% transduced cells (1:10, 1:100) showed tumoricidal effects of 58.1 and 15.1%, respectively, as compared with cultures containing only non-transduced cells (0:1). These data suggest that a single HSV-tk expressing cell is capable of conferring GCV susceptibility to between 10–50 neighboring non-transduced cells, indicating an effective bystander tumoricidal effect.

EXAMPLE 4

In Vitro Expression of IL-2 in Transduced Cells

The ability of U-251SP cells transduced with the rAAVtk-IRES-hIL2 virion to produce IL-2 was assessed as follows. Transduction was carried out with $2 \times 10^4$ human U-251SP glioma cells cultured in 1.5 cm diameter well culture dishes that were inoculated with rAAVtk-IRES-hIL2 virions at MOIs of 0, $3 \times 10^4$, $3 \times 10^5$ and $3 \times 10^6$, respectively, and then allowed to incubate for 12 hours in 500 µL of medium. The medium was then replaced, and the cells were incubated for another 48 hours in 500 µL of fresh medium. The medium was changed at 48 hour intervals. The amount of IL-2 secreted into the medium at 72 hours, 120 hours, 168 hours after inoculation was determined by solid-phase immuno-radiometric assay (IRMA) (MedGenix Diagnostics SA Fleurus, Belgium).

Figure 4:
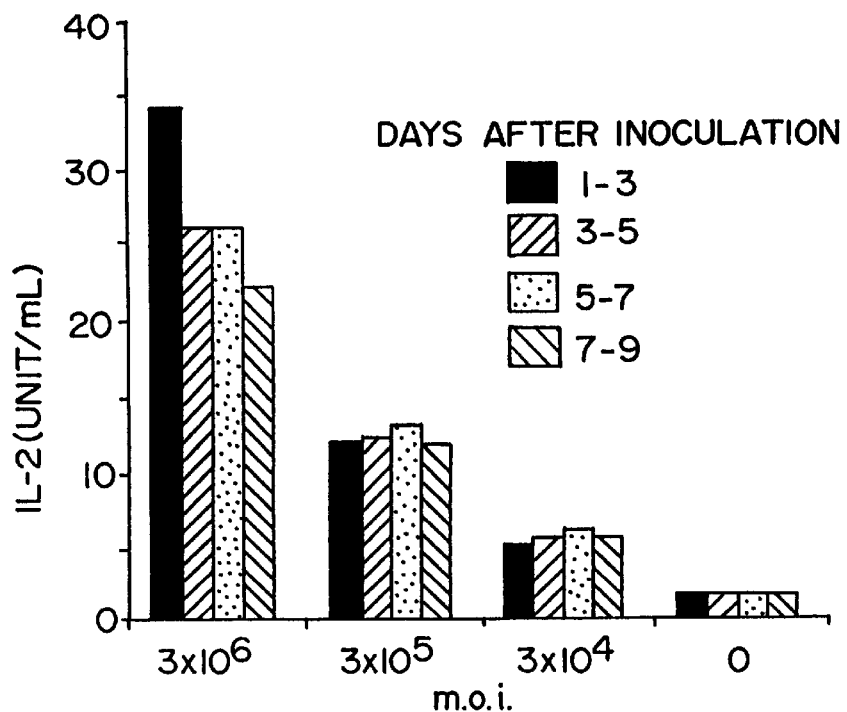
FIG. 4 depicts the results of a study of the ability of cells transduced with the human IL-2 gene to express IL-2 in vitro, as described in Example 4. In the study, $2 \times 10^4$ human U-251SP glioma cells were inoculated with rAAVTk-IRES-IL2 virions at MOIs of 0, $3 \times 10^4$, $3 \times 10^5$ and $3 \times 10^6$, and allowed to incubate for 12 hours. The amount of IL-2 secreted into the medium at 72 hours, 120 hours, 168 hours after inoculation was determined by solid-phase immunoradiometric assay (IRMA).

Referring now to FIG. 4, U-251SP cells transduced with rAAVtk-IRES-hIL2 virions expressed IL-2 in a dose-dependent manner. Particularly, at MOIs of $3 \times 10^4$, $3 \times 10^5$ and $3 \times 10^6$, stable IL-2 expression from the transduced cells was observed up to day 9.

EXAMPLE 5

In Vivo Transduction of Human U-251SP Tumor

Cells Using Recombinant AAV Virions

In order to determine the ability of the above-described recombinant AAV virions to transduce glioma tumor cells in vivo, the following studies were carried out. Experimental tumor xenografts of human U-251SP glioma cells were implanted into the brains of 6–8 week old female athymic (nu/nu) mice. Specifically, U-251SP cells were cultured in Dulbecco's modified Eagle's medium (DMEM, GIBCO, Paisley, UK) supplemented with 10% fetal calf serum, streptomycin (100 µg/mL), penicillin (100 U/mL), 2 mM L-glutamate and nonessential amino acids in 5% $CO_2$ at 37° C. The cells were harvested by trypsinizing the cells with 0.25% trypsin with gentle rocking for 5 minutes. The cells were collected, washed and resuspended in sterile PBS solution and counted prior to implantation.

The experimental animals were anesthetized by intraperitoneal injection of pentobarbital at 60–70 mg/kg body weight (NEMBUTAL®, Abbott Laboratories, North Chicago, Ill.). The head of each animal was then fixed in a stereotactic frame with an ear bar. A midline incision was made in the scalp, the skull exposed, and a burr hole was formed in the skull 3 mm lateral from the midline, 4 mm behind the bregma using a dental drill. A sterile Hamilton syringe fitted with a 26-gauge needle that was connected to the manipulating arm of the stereotactic frame was used to deliver $2 \times 10^5$ U-251SP glioma cells suspended in approximately 2 µL of PBS in approximately 0.2 µL increments over the span of 4 minutes at a depth of 3 mm below the dura mater. The needle was left in place for an additional 3 minutes and withdrawn slowly over another 3 minutes. The burr hole was sealed, and the scalp wound closed using surgical clips.

After the U-251SP xenografts were established, the following studies were carried out.

A. Transduction with rAAVLacZ Virion

Seven days after implantation, rAAVLacZ virions were injected into tumor xenografts using the same coordinates that were used for tumor implantation. More particularly, rAAVLacZ virions ($3 \times 10^{10}$ particles in 2 µL 10% glycerol/1 mM $MgCl_2$/10 mM Tris-HCl, pH 7.0) were injected into the tumors using a stereotactic apparatus as previously described. The same coordinates as in the tumor implantation were used, except that the needle was placed 0.5 mm deeper than the tumor cells and the virions were injected at four points in 0.5 µL volumes, 0.5 mm apart along the needle track as the needle was withdrawn over the span of 8 minutes. The needle was left in the tissue for an additional 3 minutes, and then slowly withdrawn over another 3 minute interval. The animals were sacrificed 4 days after transduction with the virions, and the brains were removed and fixed in 2% paraformaldehyde in PBS. In order to assess transduction efficiency, 30 µm coronal sections were stained with X-Gal and H&E to detect LacZ expression as previously described. As a result, it was found that there was approximately 30–40% transduction in tumor cells along the needle track, and no signs of toxic effects were seen in the sections analyzed.

B. Ganciclovir Treatment of Transduced Tumors

Seven days after implantation, rAAVtk-IRES-hIL2 virions were injected into tumor xenografts using the same coordinates that were used for tumor implantation. More particularly, rAAVtk-IRES-hIL2 virions ($6 \times 10^{10}$ particles in 2 µL 10% glycerol/1 mM $MgCl_2$/10 mM Tris-HCl, pH 7.0) were injected into the tumors of the experimental animals using stereotactic microinjection. As a control, rAAVLacZ virion were stereotacticly injected into the tumors of control animals. Once again, the same coordinates as in the tumor implantation were used, with the exception that the needle was placed 0.5 mm deeper than the tumor cells and the virions were injected at four points in 0.5 µL volumes, 0.5 mm apart along the needle track as the needle was withdrawn over the span of 8 minutes.

Twelve hours after the virion injection, the animals were treated intraperitoneally twice daily with either PBS (as a control) or GCV at a dose of 100 mg/kg body weight twice daily for 6 consecutive days. Four treatment groups of five animals each were established. Group (I) subjects were treated with rAAVLacZ plus PBS (e.g., Tk− G−); Group (II) subjects were treated with rAAVLacZ plus GCV (Tk− G+); Group (III) subjects were treated with rAAVTk-IRES-IL2 plus PBS (Tk+ G−); and Group (IV) subjects were treated with rAAVtk-IRES-hIL2 plus GCV (Tk+ G+). Since all of the mice were immuno-compromised (athymic) the effect of the expression of human IL-2 gene was not addressed. Members from each group were sacrificed 17 days after the initial tumor implantation, and their brains examined microscopically. More particularly, the brains were removed, fixed in 0.5% glutaraldehyde and 3% paraformaldehyde in PBS, cryoprotected in 20% sucrose and 5% glycerol in PBS, and frozen in OCT. Coronal sections (30 µM) were taken from the tumor implantation site and stained with hematoxylin and eosin. Maximal cross-sectional areas of tumors were measured by computerized morphometric analysis using IMAGE-PRO® software (available from Media Cybernetics, Silver Spring, Md.).

As a result of the study, large intracerebral tumors infiltrating adjacent brain parenchyma were seen in all of the animals in Groups (I), (II), and (III). Some animals demonstrated intra-tumoral hemorrhage but major necrotic areas were not seen in any of the control groups. Infiltration of lymphocytes was not enhanced in Group (III) in which human IL-2 was expected to be expressed (data not shown). In the Group (IV) animals, which were transduced with the HSV-tk gene and treated with GCV (Tk+ G+), tumor size was observed to be much smaller than seen in animals of the other groups. Furthermore, large areas of necrosis or hemorrhage were seen in some animals from Group (IV), indicating destruction of the tumor mass.

Figure 5:
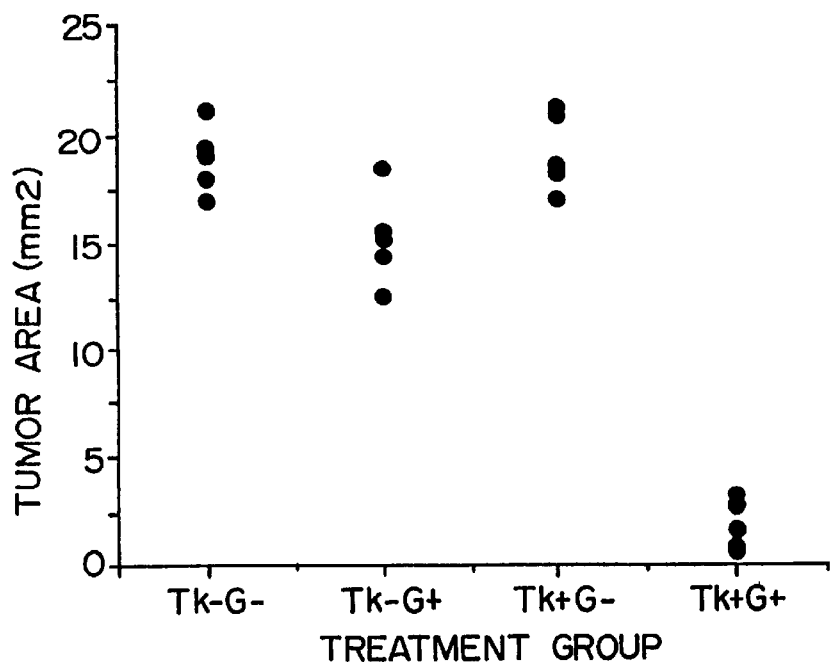
FIG. 5 depicts the cross-sectional areas of xenograft tumors following four different courses of thymidine kinase gene transduction/GCV treatment as described in Example 5B. Subjects in Group (I) were transduced with rAAVLacZ virion and treated with PBS (Tk–GCV–), those in Group (II) were transduced with rAAVLacZ virion and treated with GCV (Tk–GCV+), those in Group (III) were transduced with rAAVtk-IRES-hIL2 virion and treated with PBS (Tk+GCV–), and those in Group (IV) were transduced with rAAVtk-IRES-hIL2 virion and treated with GCV (Tk+GCV+).

Referring now to FIG. 5, although none of the Group (IV) animals had 100% tumor regression, a computerized analysis of the maximal cross sectional area of the tumors revealed a 11 fold difference between the average of treatment Group (IV) and that of the control Group (I). The average tumor cross-sectional area was also determined, and these data are reported below in Table 1. As can be seen, the average tumor cross-sectional area in Group (IV) animals was found to be 1.73±1.07 mm$^2$. By contrast, the average tumor cross-sectional areas in the other treatment groups were, respectively, 18.93±1.52 mm$^2$ in Group (I), 15.14±2.15 mm$^2$ in Group (II), and 19.06±1.79 mm$^2$ in Group (III). There was a slight reduction in the mean cross-sectional area of Group (II) when compared to the other control Groups (I) and (III) without statistical significance (p =0.12 by Student's t-test), suggesting that GCV treatment alone may have had a slight inhibitory effect on tumor growth as had been previously observed in the above-described in vitro studies.

TABLE 1

Mean Tumor Size in Animals Treated with rAAV-TK-IRES-IL2

| Viral treatment | Drug Treatment (Ganciclovir/PBS) | Mean tumor size (mm$^2$) Day 17 (n = 5/5) |
| --- | --- | --- |
| rAAV-LacZ | PBS | 18.93 ± 1.52 |
| rAAV-LacZ | GCV | 15.14 ± 2.15 |
| rAAV-TK-IRES-IL2 | PBS | 19.06 ± 1.79 |
| rAAV-TK-IRES-IL2 | GCV | 1.73 ± 1.07 |

The survival rates for animals in each of Groups (I)–(IV) which were not sacrificed were found to be as follows: Group (I) animals survived for 20.6 days on average, Group (II) animals for 22.8 days, Group (III) animals for 20.2 days, and Group (IV) animals for 28.8 days. In this regard, residual tumor xenografts proliferated rapidly soon after termination of the GCV treatment, and therefore significant survival-prolongation was not observed or expected in Group (IV).

EXAMPLE 6

In vivo Cytocidal Effect of rAAV-IFN-β on Human Glioma Tumor Xenografts in Athymic Mice The following study was carried out to assess the ability of rAAV virions expressing IFN-β (rAAV-IFN-β) to provide a therapeutic effect in an established in vivo model system. Experimental tumor xenografts of human U-251SP glioma cells were implanted into the brains of 6–8 week old athymic female Balb/c (nu/nu) mice. The U-251SP cells were prepared as described above in Example 5. To establish the tumor xenografts, the mice were anesthetized by intraperitoneal injection of pentobarbital at 60–70 mg/kg body weight (NEMBUTAL®, Abbott Laboratories, North Chicago, Ill.), and held in a stereotactic apparatus with an ear bar. An injection site was established in the skull, 3 mm lateral from the midline, 4 mm behind the bregma, and 3 mm below the dura mater. 2 µL aliquots of the U-251SP cell suspension (approximately 2×105 cells) were injected with a syringe using an INSTECH® Model 2000 microsyringe pump.

A. Effect of rAAV-IFN-β on Tumor Growth

After the U-251SP xenografts were established, a first study was conducted using two control groups (n=5), and four experimental groups (n=5). A first control group (Group I animals) received no treatment. A second control group (Group II animals) received a 2 µL volume of carrier (50 mM HEPES, 150 mM NaCl, pH 7.5) administered by stereotactic microinjection over 4 minutes along the same coordinates used for tumor implantation. Each of the four experimental groups were treated with recombinant AAV virions that were administered by stereotactic microinjection into the tumor xenografts using the same coordinates used for tumor implantation. The injections were given over 4 minutes from the stereotactic apparatus, and the needle was left in the tissue for an additional 3 minutes before being withdrawn slowly. In particular, 7 days after implantation of the glioma cells, each of the Group III animals received a single 2 µL dose of a rAAVLacZ virion preparation, 9.1× 10$^{13}$ particles/mL in a carrier (50 mM HEPES, 150 mM NaCl, pH 7.5), and the Group IV animals received six 2 µL doses, each, of the same rAAVLacZ virion preparation. The multiple injections were given every other day starting 7 days after transplantation of the glioma cells. 7 days after implantation of the glioma cells, the Group V animals received a single 2 µL dose of a rAAV-IFN-β virion preparation (1.9×10$^{13}$ particles/mL in 50 mM HEPES, 150 mM NaCl, pH 7.5), and the Group VI animals received six 2 µL doses of the same rAAV-IFN-β virion preparation, administered every-other day, and commencing 7 days after transplantation of the glioma cells.

31 days after introduction of the glioma cell xenografts, the animals from each group were sacrificed, the brains were autopsied, and gliomal tumor sizes determined. The observed tumor sizes are reported below in Table 2, wherein tumors were measured under microscope by caliper along the largest diameter. In the animals treated with rAAV-IFN-β, average production of IFN-β was determined, and is reported in Table 2 as IU IFN-β/mg brain protein. In particular, IFN-β production was assessed using an enzyme-linked immunoassay (ELISA) according to the method of Yamazaki et al. (1989) *J. Immunoassay* 10:57–73. Samples were incubated with horseradish peroxidase-labeled mouse anti-huIFN-β monoclonal antibody for 24 hours at 4° C. in 96 well culture plates onto which affinity-purified rabbit anti-huIFN-β polyclonal antibody had been coated. After washing with PBS containing 0.05% TWEEN 20®, enzyme activity was visualized with o-phenylenediamine and hydrogen peroxide. This assay can be used to detect 2.5 IU/mL or more IFN-β in a given sample.

As can be seen, the animals that received a single dose of the rAAV-IFN-β virion preparation (Group V) showed a significant reduction in tumor size when compared with both the animals receiving rAAV-LacZ virions (Groups III and IV) and control animals (Groups I and II). Further, all of the animals receiving multiple doses of the rAAV-IFN-β virion preparation (Group VI) had no measurable tumors.

TABLE 2

Mean Tumor Sizes in Animals Treated with rAAV-IFN-β

| Viral treatment | IFN-β level (IU/mg brain protein) | Mean tumor size (mm) |
|---|---|---|
| none | ND | (n = 5/5) 5.3 ± 1.5 |
| HEPES/NaCl | ND | (n = 5/5) 5.1 ± 2.0 |
| rAAV-LacZ (one injection) | ND | (n = 5/5) 4.8 ± 1.9 |
| rAAV-LacZ (six injections) | ND | (n = 5/5) 6.2 ± 2.6 |
| rAAV-IFN-β (one injection) | 0.12 ± 0.02 | (n = 5/5) 1.9 ± 0.8 |
| rAAV-IFN-β (six injections) | 0.32 ± 0.04 | (n = 0/5) — |

B. Effect of rAAV-IFN-β on Neurological Health and Animal Survival

The following study was also carried out after the U-251SP xenografts were established. Once again, two control groups (n=6), and four experimental groups (n=6) were established. The first control group (Group I animals) received no treatment. The second control group (Group II animals) received a 2 μL volume of carrier (50 mM HEPES, 150 mM NaCl, pH 7.5) administered by stereotactic microinjection over 4 minutes along the same coordinates used for tumor implantation. Each of the four experimental groups were treated with recombinant AAV virions that were administered by stereotactic microinjection into the tumor xenografts using the same coordinates used for tumor implantation. The injections were given over 4 minutes from the stereotactic apparatus, and the needle was left in the tissue for an additional 3 minutes before being withdrawn slowly. In particular, 7 days after implantation of the glioma cells, each of the Group III animals received a single 2 μL dose of a rAAVLacZ virion preparation, 9.1×10$^{13}$ particles/mL in a carrier (50 mM HEPES, 150 mM NaCl, pH 7.5), and the Group IV animals received six 2 μL doses, each, of the same rAAVLacZ virion preparation. The multiple injections were given every other day starting 7 days after transplantation of the glioma cells. 7 days after implantation of the glioma cells, the Group V animals received a single 2 μL dose of a rAAV-IFN-β virion preparation (1.9×10$^{13}$ particles/mL in 50 mM HEPES, 150 mM NaCl, pH 7.5), and the Group VI animals received six 2 μL doses of the same rAAV-IFN-β virion preparation, administered every-other day, and commencing 7 days after transplantation of the glioma cells.

After treatment, all animals were monitored daily for signs of neurological damage (assessed as spinning behavior), and the overall animal survival was determined. The results of the study are reported in Table 3. As can be seen, animals treated with a single dose of the rAAV-IFN-β virion preparation (Group V) showed a significant delay in onset of neurological symptoms relative to both the animals receiving rAAV-LacZ virions (Groups III and IV) and control animals (Groups I and II). A significant survival prolongation was also observed in the Group V animals (an approximate 50% increase in survival).

10 weeks after transplantation of the U-251SP cells, no neurological symptoms were observed in the Group VI animals (receiving multiple doses of the rAAV-IFN-β virions), and no animals had died at the termination of the study, on day 120.

TABLE 3

Neurological Symptoms in Animals Treated with rAAV-IFN-β

| Viral treatment | Days until neurological symptoms* | Survival (days) |
|---|---|---|
| none | 21.4 ± 3.5 | (n = 6) 44.33 ± 6.44 |
| HEPES/NaCl | 20.9 ± 4.4 | (n = 6) 48.00 ± 10.20 |
| rAAV-LacZ (one injection) | 22.0 ± 4.8 | (n = 6) 45.17 ± 8.18 |
| rAAV-LacZ (six injections) | 21.4 ± 7.4 | (n = 6) 42.00 ± 11.38 |
| rAAV-IFN-β (one injection) | 58.5 ± 10.8 | (n = 6) 63.67 ± 15.27 |
| rAAV-IFN-β (six injections) | — | — |

*Spinning behavior

Accordingly, novel methods of treating solid tumors have been described. Although preferred embodiments of the subject invention have been described in some detail, it is understood that obvious variations can be made without departing from the spirit and the scope of the invention as defined by the appended claims.

Deposits of Strains Useful in Practicing the Invention

A deposit of biologically pure cultures of the following strains was made with the American Type Culture Collection, 12301 Parklawn Drive, Rockville, Md., under the provisions of the Budapest Treaty. The accession number indicated was assigned after successful viability testing, and the requisite fees were paid. Access to said cultures will be available during pendency of the patent application to one determined by the Commissioner to be entitled thereto under 37 C.F.R. §1.14 and 35 U.S.C. §122. All restriction on availability of said cultures to the public will be irrevocably removed upon the granting of a patent based upon the application. Moreover, the designated deposits will be maintained for a period of thirty (30) years from the date of deposit, or for five (5) years after the last request for the deposit; or for the enforceable life of the U.S. patent, whichever is longer. Should a culture become nonviable or be inadvertently destroyed, or, in the case of plasmid-containing strains, lose its plasmid, it will be replaced with a viable culture(s) of the same taxonomic description.

These deposits are provided merely as a convenience to those of skill in the art, and are not an admission that a deposit is required. The nucleic acid sequences of these plasmids, as well as the amino sequences of the polypeptides encoded thereby, are controlling in the event of any conflict with the description herein. A license may be required to make, use, or sell the deposited materials, and no such license is hereby granted.

| Strain | Deposit Date | ATCC No. |
|---|---|---|
| pGN1909 | July 20, 1995 | 69871 |

We claim:

1. A recombinant adeno-associated virus (rAAV) virion comprising a first nucleic acid which provides target tumor cells with enhanced susceptibility to a selected cytotoxic agent, and a second nucleic acid which provides an ancillary therapeutic effect, wherein said first nucleic acid and said second nucleic acid are operably linked to expression control elements.

2. The rAAV virion of claim 1, wherein said first nucleic acid is selected from the group consisting of a gene encoding a herpes simplex virus thymidine kinase (HSV-tk), a gene encoding a cytochrome P450, a gene encoding a human deoxycytidine kinase, and a gene encoding a bacterial cytosine deaminase.

3. The rAAV virion of claim 1, wherein said second nucleic acid encodes a cytokine selected from the group consisting of alpha interferon (IFN-α), beta interferon (IFN-β), gamma interferon (IFN-γ), tumor necrosis factor (TNF), interleukin-2 (IL-2), lymphotoxin, interleukin-12, and granulocyte-macrophage colony-stimulating factor (GM-CSF).

4. The rAAV virion of claim 1, wherein said second nucleic acid is a gene encoding a tumor suppressor selected from the group consisting of p53, RB1, WT1, NF1, VHL, and APC.

5. The rAAV virion of claim 2, wherein said first nucleic acid encodes a herpes simplex virus thymidine kinase (HSV-tk).

6. The rAAV virion of claim 3, wherein the cytokine is selected from the group consisting of interleukin-2 (IL-2) and beta interferon (IFN-β).

* * * * *

UNITED STATES PATENT AND TRADEMARK OFFICE
CERTIFICATE OF CORRECTION

PATENT NO.   : 5,952,221
DATED        : September 14, 1999
INVENTOR(S)  : Gary J. Kurtzman and Peter C. Colosi It is certified that error appears in the above-identified patent and that said Letters Patent is hereby corrected as shown below:

<u>Title page,</u>
Item [75], Inventors: please replace "Gary J. Kurtzman, Menlo Park; Peter C. Colosi, Alameda, both of Calif.; Jun Yoshida; Masaaki Mizuno, Both of Nagoya, Japan; Hideho Okada, Pittsburgh, PA" with -- Gary J. Kurtzman, Menlo Park; Peter C. Colosi, Alameda, both of Calif. --

Signed and Sealed this

Third Day of September, 2002

*Attest:*

JAMES E. ROGAN
*Attesting Officer*     *Director of the United States Patent and Trademark Office*